(12) United States Patent
Decoster et al.

(10) Patent No.: US 7,504,094 B2
(45) Date of Patent: *Mar. 17, 2009

(54) COSMETIC COMPOSITIONS CONTAINING A PARTICULAR AMINOSILICONE AND A THICKENER, AND USES THEREOF

(75) Inventors: Sandrine Decoster, Saint Gratien (FR); Priscille Devin-Baudoin, Vanves (FR); Anne Sabbagh, Rueil Malmaison (FR)

(73) Assignee: L'Oreal, S.A., Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 11/706,261

(22) Filed: Feb. 15, 2007

(65) Prior Publication Data

US 2007/0154434 A1    Jul. 5, 2007

Related U.S. Application Data

(62) Division of application No. 10/290,348, filed on Nov. 8, 2002, now Pat. No. 7,220,408.

(30) Foreign Application Priority Data

Nov. 8, 2001    (FR) .................................... 01 14486

(51) Int. Cl.
    A61Q 5/02    (2006.01)
    A61Q 5/12    (2006.01)
(52) U.S. Cl. ..................................... 424/70.12; 424/70.1
(58) Field of Classification Search .................. None
    See application file for complete search history.

(56) References Cited

U.S. PATENT DOCUMENTS

| | | |
|---|---|---|
| 2,047,398 A | 7/1936 | Voss et al. |
| 2,261,002 A | 10/1941 | Ritter |
| 2,271,378 A | 1/1942 | Searle |
| 2,273,780 A | 2/1942 | Dittmar |
| 2,375,853 A | 5/1945 | Kirby et al. |
| 2,388,614 A | 11/1945 | Kirby et al. |
| 2,454,547 A | 11/1948 | Bock et al. |
| 2,528,378 A | 10/1950 | Mannheimer |
| 2,723,248 A | 11/1955 | Wright |
| 2,781,354 A | 2/1957 | Manheimer |
| 2,798,053 A | 7/1957 | Brown |
| 2,923,692 A | 2/1960 | Ackerman et al. |
| 2,961,347 A | 11/1960 | Floyd |
| 3,206,462 A | 9/1965 | McCarty |
| 3,227,615 A | 1/1966 | Korden |
| 3,472,840 A | 10/1969 | Stone et al. |
| 3,632,559 A | 1/1972 | Matter et al. |
| 3,810,977 A | 5/1974 | Levine et al. |
| 3,836,537 A | 9/1974 | Boerwinkle et al. |
| 3,874,870 A | 4/1975 | Green et al. |
| 3,910,862 A | 10/1975 | Barabas et al. |
| 3,912,808 A | 10/1975 | Sokol |
| 3,915,921 A | 10/1975 | Schlatzer, Jr. |
| 3,917,817 A | 11/1975 | Vanlerberghe et al. |
| 3,929,990 A | 12/1975 | Green et al. |
| 3,966,904 A | 6/1976 | Green et al. |
| 3,990,459 A | 11/1976 | Papantoniou |
| 4,001,432 A | 1/1977 | Green et al. |
| 4,005,193 A | 1/1977 | Green et al. |
| 4,013,787 A | 3/1977 | Varlerberghe et al. |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,008 A | 5/1977 | Sokol |
| 4,027,020 A | 5/1977 | Green et al. |
| 4,031,307 A | 6/1977 | DeMartino et al. |
| 4,070,533 A | 1/1978 | Papantoniou et al. |
| 4,075,136 A | 2/1978 | Schaper |
| 4,076,912 A | 2/1978 | Papantoniou et al. |
| 4,128,631 A | 12/1978 | Lundmark et al. |
| 4,129,711 A | 12/1978 | Viout et al. |
| 4,131,576 A | 12/1978 | Iovine et al. |
| 4,137,208 A | 1/1979 | Elliott |
| 4,157,388 A | 6/1979 | Christiansen |

(Continued)

FOREIGN PATENT DOCUMENTS

AU    200039428    2/2001

(Continued)

OTHER PUBLICATIONS

M.R. Porter, BSc, Phd, CChem, MRSC, "Handbook of Surfactants," Blackie & Son Ltd., Glasgow and London, 1991, pp. 116-178.

(Continued)

*Primary Examiner*—Jyothsna A Venkat
(74) *Attorney, Agent, or Firm*—Finnegan, Henderson, Farabow, Garrett, & Dunner, L.L.P.

(57) ABSTRACT

A novel cosmetic composition comprising, in a cosmetically acceptable medium, at least one aminosilicone of as defined herein having, for example, a contact angle ranging from 90° to 180° and at least one thickener, being able to afford at least one improved cosmetic property (such as lightness, disentangling, volume and sheen) and/or at least one of long-lasting and remanent effects, as well as uses of the composition, such as for washing and/or conditioning keratin materials such as the hair or the skin.

17 Claims, No Drawings

U.S. PATENT DOCUMENTS

| | | |
|---|---|---|
| 4,165,367 A | 8/1979 | Chakrabarti |
| 4,172,887 A | 10/1979 | Vanlerberghe et al. |
| 4,217,914 A | 8/1980 | Jacquet et al. |
| 4,223,009 A | 9/1980 | Chakrabarti |
| 4,237,243 A | 12/1980 | Quack et al. |
| 4,277,581 A | 7/1981 | Vanlerberghe et al. |
| 4,282,203 A | 8/1981 | Jacquet et al. |
| 4,349,532 A | 9/1982 | Vanlerberghe et al. |
| 4,509,949 A | 4/1985 | Huang et al. |
| 4,591,610 A | 5/1986 | Grollier |
| 4,608,250 A | 8/1986 | Jacquet et al. |
| 4,673,568 A | 6/1987 | Grollier et al. |
| 4,693,935 A | 9/1987 | Mazurek |
| 4,702,906 A | 10/1987 | Jacquet et al. |
| 4,710,314 A | 12/1987 | Madrange et al. |
| 4,719,099 A | 1/1988 | Grollier et al. |
| 4,719,282 A | 1/1988 | Nadolsky et al. |
| 4,728,571 A | 3/1988 | Clemens et al. |
| 4,761,273 A | 8/1988 | Grollier et al. |
| 4,770,873 A | 9/1988 | Wolfram et al. |
| 4,839,166 A | 6/1989 | Grollier et al. |
| 4,957,732 A | 9/1990 | Grollier et al. |
| 4,972,037 A | 11/1990 | Garbe et al. |
| 4,996,059 A | 2/1991 | Grollier et al. |
| 5,009,880 A | 4/1991 | Grollier et al. |
| 5,057,311 A | 10/1991 | Kamegai et al. |
| 5,061,289 A | 10/1991 | Clausen et al. |
| 5,077,040 A | 12/1991 | Bergmann et al. |
| 5,085,860 A | 2/1992 | Junino et al. |
| 5,089,252 A | 2/1992 | Grollier et al. |
| 5,106,612 A | 4/1992 | Maignan et al. |
| 5,139,037 A | 8/1992 | Grollier et al. |
| 5,154,918 A | 10/1992 | Maignan et al. |
| 5,196,189 A | 3/1993 | Jacquet et al. |
| 5,210,324 A | 5/1993 | Farrar et al. |
| 5,340,367 A | 8/1994 | Schultz et al. |
| 5,344,464 A | 9/1994 | Madrange et al. |
| 5,380,340 A | 1/1995 | Neunhoeffer et al. |
| 5,466,878 A | 11/1995 | Junino et al. |
| 5,534,267 A | 7/1996 | Neunhoeffer et al. |
| 5,538,717 A | 7/1996 | De La Poterie |
| 5,583,257 A | 12/1996 | Junino et al. |
| 5,626,840 A | 5/1997 | Thomaides et al. |
| 5,663,366 A | 9/1997 | Neunhoeffer et al. |
| 5,708,151 A | 1/1998 | Mockli |
| 5,741,337 A | 4/1998 | Bone et al. |
| 5,756,076 A | 5/1998 | Cervantes et al. |
| 5,766,576 A | 6/1998 | Lowe et al. |
| 5,773,611 A | 6/1998 | Zysman et al. |
| 5,833,997 A | 11/1998 | Mahieu et al. |
| 5,925,341 A | 7/1999 | Cervantes et al. |
| 5,958,392 A | 9/1999 | Grollier et al. |
| 5,976,195 A | 11/1999 | De La Mettrie et al. |
| 6,010,541 A | 1/2000 | De La Mettrie |
| 6,071,504 A | 6/2000 | Kawai et al. |
| 6,099,592 A | 8/2000 | Vidal et al. |
| 6,099,593 A | 8/2000 | Terranova et al. |
| 6,143,286 A | 11/2000 | Bhambhani et al. |
| 6,177,090 B1 | 1/2001 | Dubief et al. |
| 6,179,881 B1 | 1/2001 | Henrion et al. |
| 6,214,326 B1 | 4/2001 | Dupuis |
| 6,254,646 B1 | 7/2001 | De La Mettrie et al. |
| 6,260,556 B1 | 7/2001 | Legrand et al. |
| 6,284,003 B1 | 9/2001 | Rose et al. |
| 6,319,959 B1 | 11/2001 | Mougin et al. |
| 6,372,876 B1 | 4/2002 | Kim et al. |
| 6,395,265 B1 | 5/2002 | Mougin et al. |
| 6,471,953 B1 | 10/2002 | Nguyen et al. |
| 6,479,042 B1 | 11/2002 | Nguyen et al. |
| 6,506,373 B1 | 1/2003 | Dannecker et al. |
| 6,511,669 B1 | 1/2003 | Garnier et al. |
| 6,582,477 B1 | 6/2003 | Plos |
| 6,613,313 B2 | 9/2003 | Kimura |
| 6,770,271 B2 | 8/2004 | Mondet et al. |
| 6,824,764 B2 * | 11/2004 | Devin-Baudoin et al. .. 424/70.1 |
| 6,824,765 B2 * | 11/2004 | Gawtrey et al. ............ 424/70.1 |
| 6,846,333 B2 | 1/2005 | Legrand et al. |
| 6,916,467 B2 | 7/2005 | Devin-Baudoin et al. |
| 7,128,902 B2 * | 10/2006 | Legrand et al. ......... 424/70.122 |
| 7,135,167 B2 * | 11/2006 | Legrand et al. ......... 424/70.122 |
| 7,138,109 B2 * | 11/2006 | Devin-Baudoin et al. ..... 424/62 |
| 7,220,408 B2 * | 5/2007 | Decoster et al. .......... 424/70.12 |
| 7,223,385 B2 * | 5/2007 | Gawtrey et al. .......... 424/70.12 |
| 2002/0006389 A1 | 1/2002 | Restle et al. |
| 2002/0187117 A1 | 12/2002 | Devin-Baudoin et al. |

FOREIGN PATENT DOCUMENTS

| | | |
|---|---|---|
| EP | 0 122 324 | 10/1984 |
| EP | 0 216 479 | 4/1987 |
| EP | 0 227 994 | 7/1987 |
| EP | 0 337 354 | 10/1989 |
| EP | 0 342 834 | 11/1989 |
| EP | 0 412 704 | 2/1991 |
| EP | 0 412 707 | 2/1991 |
| EP | 0 486 135 | 5/1992 |
| EP | 0 582 152 | 2/1994 |
| EP | 0 619 111 | 10/1994 |
| EP | 0 646 572 | 4/1995 |
| EP | 0 890 355 | 1/1999 |
| EP | 0 974 335 | 1/2000 |
| FR | 1 492 597 | 8/1967 |
| FR | 1 580 545 | 9/1969 |
| FR | 1 583 363 | 10/1969 |
| FR | 2 077 143 | 10/1971 |
| FR | 2 080 759 | 11/1971 |
| FR | 2 162 025 | 7/1973 |
| FR | 2 190 406 | 2/1974 |
| FR | 2 252 840 | 6/1975 |
| FR | 2 280 361 | 12/1976 |
| GB | 0 839 805 | 6/1960 |
| GB | 0 922 457 | 4/1963 |
| GB | 1 021 400 | 3/1966 |
| GB | 1 026 978 | 4/1966 |
| GB | 1 153 196 | 5/1969 |
| GB | 1 486 576 | 9/1977 |
| GB | 1 546 809 | 5/1979 |
| GB | 2 141 454 | 12/1984 |
| GB | 2 165 550 | 4/1986 |
| GB | 2 058 103 | 4/1991 |
| WO | WO 93/23446 | 11/1993 |
| WO | WO 94/07844 | 4/1994 |
| WO | WO 94/10131 | 5/1994 |
| WO | WO 95/00578 | 1/1995 |
| WO | WO 95/01772 | 1/1995 |
| WO | WO 95/15144 | 6/1995 |
| WO | WO 95/16665 | 6/1995 |

OTHER PUBLICATIONS

Kirk-Othmer, Encyclopedia of Chemical Technology,: Third edition, vol. 22, John Wiley & Sons, pp. 332-433, 1982.
English language Derwent Abstract of EP 0 080 976, Jun. 8, 1983.
English language Derwent Abstract of FR 2 077 143, Oct. 15, 1971.
English language Derwent Abstract of FR 2 080 759, Nov. 19, 1971.
English language Derwent Abstract of FR 2 320 330, Mar. 4, 1977.
English language Derwent Abstract of FR 2 336 434, Jul. 22, 1977.
English language Patent Abstract of JP 2001-10935, Jan. 16, 2001.
"Encyclopedia of Chemical Technology", Kirk-Othmer, Third Edition, 1982, vol. 15, pp. 439-458.
"Encyclopedia of Chemical Technology", Kirk-Othmer, Third Edition, 1982, vol. 3, pp. 896-900.
"Industrial Gums—Polysaccharides and their Derivatives", edited by Roy L. Whistler, Second Edition, Academic Press, 1973.

"Polymers in Nature", E.A. MacGregor & C.T. Greenwood, John Wiley & Sons, Chapter 6, pp. 240-328, 1980.
"Volatile Silicone Fluids for Cosmetic Formulations", Cosmetics and Toiletries, vol. 91, Jan. 1976, pp. 27-32.
Copending U.S. Appl. No. 10/290,149, filed Nov. 8, 2002.
Copending U.S. Appl. No. 10/290,159, filed Nov. 8, 2002.
Copending U.S. Appl. No. 10/290,189, filed Nov. 8, 2002.
Copending U.S. Appl. No. 10/290,192, filed Nov. 8, 2002.
Copending U.S. Appl. No. 10/290,208, filed Nov. 8, 2002; issued as U.S. Patent No. 7,128,902.
Copending U.S. Appl. No. 10/290,226, filed Nov. 8, 2002.
Copending U.S. Appl. No. 10/290,341, filed Nov. 8, 2002; issued as U.S. Patent No. 7,138,109.
Copending U.S. Appl. No. 10/290,342, filed Nov. 8, 2002.
Copending U.S. Appl. No. 10/290,343, filed Nov. 8, 2002.
Copending U.S. Appl. No. 10/290,345, filed Nov. 8, 2002.
Copending U.S. Appl. No. 10/290,372, filed Nov. 8, 2002; issued as U.S. Patent No. 7,135,167.
Copending U.S. Appl. No. 10/290,409, filed Nov. 8, 2002.
Copending U.S. Appl. No. 11/158,014, filed Jun. 22, 2005.
English language Derwent Abstract of DE 197 54 053, Jun. 10, 1999.
English language Derwent Abstract of DE 42 29 922, Mar. 10, 1994.
English language Derwent Abstract of DE 44 02 929, Jun. 22, 1995.
English language Derwent Abstract of DE 44 20 736, Aug. 10, 1995.
English language Derwent Abstract of DE 44 24 530, Jan. 18, 1996.
English language Derwent Abstract of DE 44 24 533, Jan. 18, 1996.
English language Derwent Abstract of EP 0 225 261, Jun. 10, 1987.
English language Derwent Abstract of EP 0 368 763, May 16, 1990.
English language Derwent Abstract of EP 0 765 655, Apr. 2, 1987.
English language Derwent Abstract of FR 2 679 448, Jan. 29, 1993.
English language Derwent Abstract of FR 2 679 558, Jan. 29, 1993.
English language Derwent Abstract of JP 2001-10936, Jan. 16, 2001.
English language Derwent Abstract of JP 2-250814, Oct. 8, 1990.
English language Derwent Abstract of JP 4-154713, May 27, 1992.
English language Derwent Abstract of JP 8-157340, Jun. 18, 1996.
English language Derwent Abstract of JP 9-151120, Jun. 10, 1997.
English language JAPIO Abstract of JP 2-019576, Jan. 23, 1990.
English language JAPIO Abstract of JP 9-110659, Apr. 28, 1997.
French Search Report for FR 0 114 468, dated Aug. 8, 2002, related to U.S. Appl. No. 10/290,341.
French Search Report for FR 0 114 469, dated Aug. 22, 2002, related to U.S. Appl. No. 10/290,345.
French Search Report for FR 0 114 470, dated Sep. 18, 2002, related to U.S. Appl. No. 10/290,208.
French Search Report for FR 0 114 472, dated Aug. 30, 2002, related to U.S. Appl. No. 10/290,342.
French Search Report for FR 0 114 473, dated Sep. 16, 2002, related to U.S. Appl. No. 10/290,192.
French Search Report for FR 0 114 474, dated Aug. 8, 2002, related to U.S. Appl. No. 10/290,372.
French Search Report for FR 0 114 476, dated Sep. 20, 2002, related to U.S. Appl. No. 10/290,409.
French Search Report for FR 0 114 477, dated Sep. 20, 2002, related to U.S. Appl. No. 10/290,409.
French Search Report for FR 0 114 478, dated Sep. 18, 2002, related to U.S. Appl. No. 10/290,189.
French Search Report for FR 0 114 479, dated Sep. 16, 2002, related to U.S. Appl. No. 10/290,148.
French Search Report for FR 0 114 480, dated Aug. 9, 2002, related to U.S. Appl. No. 10/290,226.
French Search Report for FR 0 114 481, dated Sep. 4, 2002, related to U.S. Appl. No. 10/290,159.
French Search Report for FR 0 114 482, dated Aug. 28, 2002, related to U.S. Appl. No. 10/290,226.
French Search Report for FR 0 114 484, dated Sep. 4, 2002, related to U.S. Appl. No. 10/290,149.
French Search Report for FR 0 114 485, dated Aug. 29, 2002, related to U.S. Appl. No. 10/290,343.
French Search Report for FR 0 114 486, dated Sep. 23, 2002, related to U.S. Appl. No. 10/290,348.
Office Action in co-pending U.S. Appl. No. 10/290,149, dated Apr. 30, 2004.
Office Action in co-pending U.S. Appl. No. 10/290,149, dated Nov. 4, 2004.
Office Action in co-pending U.S. Appl. No. 10/290,189, dated Feb. 16, 2006.
Office Action in co-pending U.S. Appl. No. 10/290,192, dated Jun. 23, 2006.
Office Action in co-pending U.S. Appl. No. 10/290,192 dated Jan. 11, 2006.
Office Action in co-pending U.S. Appl. No. 10/290,208, dated Jan. 11, 2006.
Office Action in co-pending U.S. Appl. No. 10/290,226, dated Apr. 19, 2006.
Office Action in co-pending U.S. Appl. No. 10/290,341 dated Jan. 11, 2006.
Office Action in co-pending U.S. Appl. No. 10/290,342, dated Jan. 25, 2006.
Office Action in co-pending U.S. Appl. No. 10/290,342, dated Jul. 10, 2006.
Office Action in co-pending U.S. Appl. No. 10/290,343, dated Jan. 25, 2006.
Office Action in co-pending U.S. Appl. No. 10/290,345, dated Feb. 9, 2006.
Office Action in co-pending U.S. Appl. No. 10/290,372, dated Jan. 10, 2006.
Office Action in co-pending U.S. Appl. No. 10/290,409, dated Apr. 19, 2006.
P.D. Dorgan "Waxes in Cosmetics", Drug and Cosmetic Industry, Dec. 1983, pp. 30-33.

* cited by examiner

COSMETIC COMPOSITIONS CONTAINING A PARTICULAR AMINOSILICONE AND A THICKENER, AND USES THEREOF

This is a divisional application of application Ser. No. 10/290,348, filed Nov. 8, 2002, now U.S. Pat. No. 7,220,408 which claims the benefit of French Patent Application No. 01 14486, filed Nov. 8, 2001, all of which are incorporated herein by reference.

Disclosed herein is a novel cosmetic composition comprising, in a cosmetically acceptable medium, at least one particular aminosilicone and at least one thickener.

It is well known that hair that has been sensitized (i.e. damaged and/or embrittled) to varying degrees by the action of atmospheric agents or by the action of mechanical or chemical treatments, such as dyeing, bleaching and/or permanent-waving, may often be difficult to disentangle and to style, and may lack softness.

It has already been recommended, in compositions for washing or caring for keratin materials such as the hair, to use conditioners, such as cationic polymers and silicones, to facilitate the disentangling of the hair and to impart softness and suppleness thereto. However, at least one of the cosmetic advantages mentioned above can unfortunately also be accompanied, on dried hair, by certain cosmetic effects considered undesirable, namely a lank effect on the hairstyle (lack of lightness of the hair) and a lack of smoothness (hair not uniform from the root to the end).

In addition, the use of aminosilicones for this purpose can have various drawbacks. On account of their strong affinity for hair, some of these silicones can become deposited in considerable amount during repeated use, and can lead to adverse effects such as an unpleasant, laden (charged or loaded) feel, stiffening of the hair and adhesion between fibres, affecting the styling. These drawbacks can be accentuated in the case of fine hair, which lacks liveliness and volume.

Furthermore, although aminosilicone microemulsions show particularly good performance, they can be difficult to formulate in hair compositions, these compositions being found to be of lower performance, for example by, showing poor remanence.

In summary, it is found that the current cosmetic compositions containing aminosilicones are not always entirely satisfactory.

The inventors have now discovered that the combination of at least one particular aminosilicone with at least one thickener makes it possible to overcome at least one of these drawbacks.

The inventors have now found that a composition comprising at least one aminosilicone as defined below and at least one thickener, makes it possible to limit or even eliminate at least one of the lack of sheen, smoothness and softness of the hair, while at the same time retaining at least one of the other advantageous cosmetic properties associated with compositions containing a silicone.

The composition disclosed herein can lead to an optimization of the deposition of silicone onto keratin materials.

The composition disclosed herein can also afford at least one improved cosmetic property (such as lightness, softness, disentangling, a natural feel together with great ease of styling, and sheen) and, what is more, the effects can be persistent and remanent to, for example, withstand shampooing several times.

The composition disclosed herein when applied to the skin, such as in the form of a bubble bath or shower gel, can afford an improvement in the softness of the skin.

Thus, novel cosmetic compositions are now proposed, comprising, in a cosmetically acceptable medium, at least one aminosilicone as defined below and at least one thickener.

Another new embodiment relates to the inclusion of at least one aminosilicone as defined below, in, or for the manufacture of, a cosmetic composition comprising at least one thickener.

Another new embodiment relates to a composition comprising at least one aminosilicone as defined below and at least one thickener, as well as methods, for conditioning a keratin material.

Another new embodiment relates to a composition comprising at least one aminosilicone as defined below and at least one thickener, as well as methods, for improving the lightness, softness, sheen and/or disentangling, and/or facilitating the styling of a keratin material.

Another new embodiment relates to a composition comprising at least one aminosilicone as defined below and at least one thickener, as well as methods, for improving the remanence of, for example, the conditioning effects with respect to shampooing.

Various illustrative new embodiments will now be described in detail. All the meanings and definitions of the compounds given below are valid for all new embodiments.

In context, the term "thickener" means any agent whose function is to increase the viscosity of the composition.

The term "keratin materials" means hair, eyelashes, eyebrows, skin, nails, mucous membranes or scalp.

In one new embodiment, the at least one aminosilicone is chosen from aminosilicones of formulae (I) and (II) below:

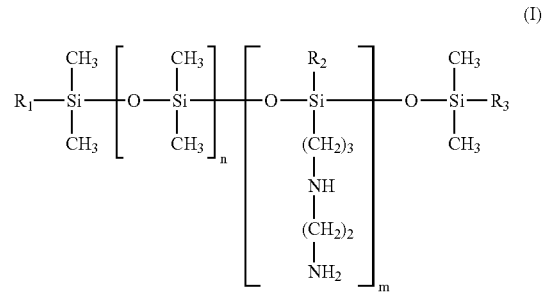

in which:

m and n are numbers such that the sum (n+m) ranges, from 1 to 1000, further, for example, from 50 to 250 and even further, for example, from 100 to 200, n is a number ranging from 0 to 999, further, for example, from 49 to 249 and even further, for example, from 125 to 175, and m is a number ranging from 1 to 1000, further, for example, from 1 to 10 and even further, for example, from 1 to 5;

$R_1$, $R_2$ and $R_3$, which may be identical or different, are chosen from hydroxyl and $C_1$-$C_4$ alkoxy radicals, wherein at least one of the radicals $R_1$, $R_2$, and $R_3$, for example, is chosen from $C_1$-$C_4$ alkoxy radicals.

In one embodiment, the alkoxy radical is a methoxy radical.

The hydroxyl/alkoxy molar ratio may range, for example, from 0.2:1 to 0.4:1, further, for example, from 0.25:1 to 0.35:1 and even further, for example, is equal to 0.3:1.

The weight-average molecular mass of the at least one aminosilicone of formula (I) ranges, for example, from 2000 to 1 000 000 and further, for example, from 3500 to 200 000.

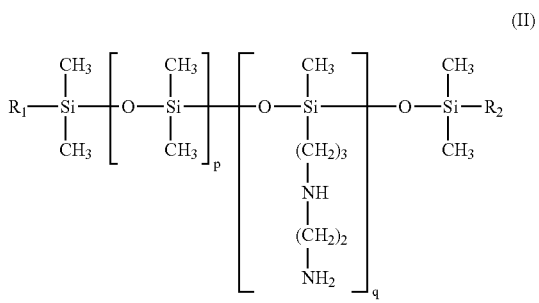

in which:

p and q are numbers such that the sum (p+q) ranges, from 1 to 1000, further, for example, from 50 to 350 and even further, for example, from 150 to 250, p is a number ranging, from 0 to 999, further, for example, from 49 to 349 and even further, for example, from 159 to 239, and q is a number ranging, for example, from 1 to 1000, further, for example, from 1 to 10 and even further, for example, from 1 to 5;

$R_1$, and $R_2$, which are different, are chosen from hydroxyl and $C_1$-$C_4$ alkoxy radicals, wherein at least one of the radicals $R_1$, and $R_2$, for example, is chosen from $C_1$-$C_4$ alkoxy radicals.

In one embodiment, the alkoxy radical is a methoxy radical.

The hydroxyl/alkoxy molar ratio may range, for example, from 1:0.8 to 1:1.1, further, for example, from 1:0.9 to 1:1 and even further, for example, is equal to 1:0.95.

The weight-average molecular mass of the at least one aminosilicone of formula (II) ranges, for example, from 2000 to 200 000, further, for example, from 5000 to 100 000 and even further, for example, from 10 000 to 50 000.

The weight-average molecular mass of the at least one aminosilicone is measured by Gel Permeation Chromatography (GPC) at room temperature, as polystyrene equivalents. The columns used are styragel μ columns. The eluent is THF and the flow rate is 1 ml/minute. 200 μl of a solution at 0.5% by weight of silicone in THF are injected. The detection is performed by refractometry and UV-metry.

The commercial products corresponding to the at least one aminosilicone of formula (I) or (II) can include in their composition at least one other aminosilicone whose structure is different from the formulae (I) and (II).

A product containing the at least one aminosilicone of formula (I), is sold by the company Wacker under the name Belsil ADM 652®.

Products containing aminosilicones of formula (II), mention may be made, for example, of a product sold by Wacker under the name Fluid WR 1300®.

In one new embodiment, the at least one aminosilicone is used in the form of an oil-in-water emulsion. The oil-in-water emulsion may comprise at least one surfactant.

The at least one surfactant may be of any nature, for example, cationic and/or nonionic.

The number-average size of the at least one aminosilicone particle (i.e., the mean particle size of the at least one aminosilicone) in the emulsion ranges, for example, from 3 to 500 nanometres. Such particle sizes are measured with a laser granulometer.

For example, the mean particle size of the at least one aminosilicone of formula (II) in the microemulsion, ranges, for example, from 5 to 60 nanometres and further, for example, from 10 to 50 nanometres. Such particle sizes can be measured by one skilled in the art using ordinary techniques.

An example of the microemulsions of the aminosilicone of formula (II) is sold under the name Finish CT 96 E® or SLM 28020® by the company Wacker.

In one embodiment, the at least one aminosilicone is chosen, for example, such that the contact angle with water of a hair treated with a composition comprising 2% (active materials) of the said at least one aminosilicone ranges, for example, from 90 to 180° and further, for example, from 90 to 130°. As used herein, a range "from x to y" includes within the range the endpoints x and y.

To measure the contact angle, the at least one aminosilicone is, for example, dissolved or dispersed in a solvent for the aminosilicone or for the aminosilicone emulsion, for example, hexamethyldisiloxane or water depending on the hydrophilicity of the silicone.

In another embodiment, the composition comprising the at least one aminosilicone chosen from aminosilicones of formulae (I) and (II) is such that the contact angle of a hair treated with the said composition ranges, for example, from 90 and 180° and further, for example, from 90 to 130°.

The contact angle measurement is based on immersion of a hair in distilled water. The measurement includes evaluating the force exerted by the water on the hair during its immersion in distilled water and the force exerted by the water on the hair during its removal. The forces thus measured are directly linked to the contact angle θ existing between the water and the surface of the hair. The hair is hydrophilic when the angle θ ranges from 0 to less than 90°, and hydrophobic when the angle θ ranges from 90° to 180°.

The test is carried out with locks of natural hair that have been bleached under the same conditions and then washed.

Each 1 g lock is placed in a crystallizing dish 75 mm in diameter and then covered uniformly with 5 ml of the formulation to be tested. The lock is thus left for 15 minutes at room temperature and then rinsed with distilled water for 30 seconds. The drained lock is left in the open air until it is completely dry.

For each evaluation, 10 hair strands that have undergone the same treatment are analysed. Each sample, attached to a precision microbalance, is immersed via its end in a container filled with distilled water. This DCA balance ("Dynamic Contact Angle Analyser"), from the company Cahn Instruments, allows the force (F) exerted by the water on the hair to be measured.

In parallel, the perimeter (P) of the hair is measured by means of observation by microscope.

The mean wettability force on 10 hair strands and the section of the analysed hairs make it possible to obtain the contact angle of the hair on the water, according to the formula:

$$F = P * \lceil lv * \cos\theta$$

where F is the wettability force expressed in Newtons, P is the perimeter of the hair in metres, ⌈lv is the liquid/water vapour interface tension in $J/m^2$ and θ is the contact angle.

The product SLM 28020® from Wacker at 12% in water (i.e. 2% aminosilicone as active materials) gives a contact angle of 93° according to the test indicated above.

The product Belsil ADM 652 from Wacker at 2% in hexamethyldisiloxane (i.e. 2% aminosilicone as active materials) gives a contact angle of 111° according to the test indicated above.

The at least one aminosilicone chosen from aminosilicones of formulae (I) and (II) is, for example, used in an amount ranging from 0.01% to 20% by weight relative to the total weight of the composition. As a further example, this amount ranges from 0.1% to 15% by weight and, further, for example, from 0.5% to 10% by weight, relative to the total weight of the composition.

The at least one thickener is chosen, for example, from:
(i) associative thickeners;
(ii) crosslinked acrylic acid homopolymers;
(iii) crosslinked copolymers of (meth)acrylic acid and of ($C_1$-$C_6$)alkyl acrylate;
(iv) nonionic homopolymers and copolymers containing ethylenically unsaturated monomers of ester and amide type;
(v) ammonium acrylate homopolymers and copolymers of ammonium acrylate and of acrylamide;
(vi) polysaccharides; and
(vii) $C_{12}$-$C_{30}$ fatty alcohols.

(i) As used herein, the expression "associative thickener" means an amphiphilic thickener comprising both hydrophilic units and hydrophobic units, for example, at least one $C_8$-$C_{30}$ fatty chain and at least one hydrophilic unit.

Representative associative thickeners that may be used are associative polymers chosen from:
(i) nonionic amphiphilic polymers comprising at least one fatty chain and at least one hydrophilic unit;
(ii) anionic amphiphilic polymers comprising at least one hydrophilic unit and at least one fatty-chain unit;
(iii) cationic amphiphilic polymers comprising at least one hydrophilic unit and at least one fatty-chain unit; and
(iv) amphoteric amphiphilic polymers comprising at least one hydrophilic unit and at least one fatty-chain unit;

the fatty chain containing from 10 to 30 carbon atoms.

The nonionic amphiphilic polymers comprising at least one fatty chain and at least one hydrophilic unit may, for example, be chosen from:

(1) celluloses modified with groups comprising at least one fatty chain; examples that may be mentioned include:
  hydroxyethylcelluloses modified with groups comprising at least one fatty chain chosen from alkyl, arylalkyl and alkylaryl groups, and in which the alkyl groups are, for example, $C_8$-$C_{22}$, such as the product Natrosol Plus Grade 330 CS ($C_{16}$ alkyls) sold by the company Aqualon, and the product Bermocoll EHM 100 sold by the company Berol Nobel, and
  celluloses modified with polyalkylene glycol alkylphenyl ether groups, such as the product Amercell Polymer HM-1500 (polyethylene glycol (15) nonylphenyl ether) sold by the company Amerchol.
(2) hydroxypropyl guars modified with groups comprising at least one fatty chain, such as the product Esaflor HM 22 ($C_{22}$ alkyl chain) sold by the company Lamberti, and the products Miracare XC95-3 ($C_{14}$ alkyl chain) and RE205-1 ($C_{20}$ alkyl chain) sold by the company Rhodia Chimie.
(3) polyether urethanes comprising at least one fatty chain, such as $C_{10}$-$C_{30}$ alkyl or alkenyl groups, for instance the products Elfacos T 210 and Elfacos T 212 sold by the company Akzo or the products Aculyn 44 and Aculyn 46 sold by the company Rohm & Haas.
(4) copolymers of vinylpyrrolidone and of fatty-chain hydrophobic monomers; examples that may be mentioned include:
  the products Antaron V216 and Ganex V216 (vinylpyrrolidone/hexadecene copolymer) sold by the company I.S.P.,
  the products Antaron V220 and Ganex V220 (vinylpyrrolidone/eicosene copolymer) sold by the company I.S.P.
(5) copolymers of $C_1$-$C_6$ alkyl acrylates or methacrylates and of amphiphilic monomers comprising at least one fatty chain, such as the oxyethylenated methyl methacrylate/stearyl acrylate copolymer sold by the company Goldschmidt under the name Antil 208.
(6) copolymers of hydrophilic acrylates or methacrylates and of hydrophobic monomers comprising at least one fatty chain, such as polyethylene glycol methacrylate/lauryl methacrylate copolymer.

The anionic amphiphilic polymers comprising at least one hydrophilic unit and at least one fatty-chain unit, may, for example, be chosen from those comprising at least one fatty-chain allyl ether unit and at least one hydrophilic unit comprising an ethylenic unsaturated anionic monomeric unit, for example, a vinylcarboxylic acid unit and further, for example, chosen from units derived from acrylic acids, methacrylic acids and mixtures thereof, wherein the fatty-chain allyl ether unit corresponds to the monomer of formula (III) below:

$$CH_2=C(R1)CH_2OB_nR \qquad (III)$$

in which R1 is chosen from H and $CH_3$, B is an ethyleneoxy radical, n is chosen from zero and integers ranging from 1 to 100, R is chosen from hydrocarbon-based radicals chosen from alkyl, arylalkyl, aryl, alkylaryl and cycloalkyl radicals, comprising from 10 to 30 carbon atoms, and, further, for example, from 10 to 24 carbon atoms and even further, for example, from 12 to 18 carbon atoms.

In one embodiment, a unit of formula (III) is, for example, a unit in which R1 can be H, n can be equal to 10 and R can be a stearyl ($C_{18}$) radical.

Anionic amphiphilic polymers of this type are described and prepared, according to an emulsion polymerization process, in patent EP-0 216 479 B2.

In one embodiment, anionic amphiphilic polymers are, for example, polymers formed from 20% to 60% by weight of acrylic acid and/or of methacrylic acid, from 5% to 60% by weight of lower alkyl (meth)acrylates, from 2% to 50% by weight of fatty-chain allyl ether of formula (III), and from 0% to 1% by weight of a crosslinking agent which is a well-known copolymerizable unsaturated polyethylenic monomer, for example, diallyl phthalate, allyl (meth)acrylate, divinylbenzene, (poly)ethylene glycol dimethacrylate and methylenebisacrylamide.

Examples of such polymers are crosslinked terpolymers of methacrylic acid, of ethyl acrylate and of polyethylene glycol (10 EO) stearyl ether (Steareth-10), such as those sold by the company Ciba under the names Salcare SC 80 and Salcare SC 90, which are aqueous 30% emulsions of a crosslinked terpolymer of methacrylic acid, of ethyl acrylate and of steareth-10 allyl ether (40/50/10).

The anionic amphiphilic polymers may further be chosen, for example, from those comprising at least one hydrophilic unit of unsaturated olefinic carboxylic acid type, and at least one hydrophobic unit of the type such as a ($C_{10}$-$C_{30}$) alkyl ester of an unsaturated carboxylic acid. The hydrophilic unit of unsaturated olefinic carboxylic acid type corresponds to, for example, the monomer of formula (IV) below:

$$H_2C=\underset{R^1}{\overset{}{C}}-\underset{O}{\overset{}{C}}-OH \qquad (IV)$$

in which $R^1$ is chosen from H, $CH_3$, and $C_2H_5$, i.e. acrylic acid, methacrylic acid and ethacrylic acid units. And the hydrophobic unit of the type such as a ($C_{10}$-$C_{30}$) alkyl ester of an unsaturated carboxylic acid corresponds to, for example, the monomer of formula (V) below:

(V)

in which $R^1$ is chosen from H, $CH_3$, and $C_2H_5$ (i.e. acrylate, methacrylate and ethacrylate units) and is, for example, chosen from, for example, H (acrylate units) and $CH_3$ (methacrylate units), $R^2$ is chosen from $C_{10}$-$C_{30}$ alkyl radicals, for example, $C_{12}$-$C_{22}$ alkyl radical.

Examples of ($C_{10}$-$C_{30}$)alkyl esters of unsaturated carboxylic acids include lauryl acrylate, stearyl acrylate, decyl acrylate, isodecyl acrylate, and dodecyl acrylate, and the corresponding methacrylates, lauryl methacrylate, stearyl methacrylate, decyl methacrylate, isodecyl methacrylate and dodecyl methacrylate.

Anionic amphiphilic polymers of this type are disclosed and prepared, for example, according to U.S. Pat. Nos. 3,915,921 and 4,509,949.

Representative anionic amphiphilic polymers that can be used may further be chosen from polymers formed from a mixture of monomers comprising:

(i) acrylic acid, an ester of formula (VI) below:

(VI)

in which $R^1$ is chosen from H and $CH_3$, $R^2$ is chosen from $C_{10}$-$C_{30}$ alkyl radicals, such as alkyl radicals comprising from 12 to 22 carbon atoms, and a crosslinking agent; such as polymers derived from 95% to 60% by weight of the acrylic acid (hydrophilic unit), 4% to 40% by weight of $C_{10}$-$C_{30}$ alkyl acrylate (hydrophobic unit), and 0% to 6% by weight of crosslinking polymerizable monomer, or polymers derived from 98% to 96% by weight of the acrylic acid (hydrophilic unit), 1% to 4% by weight of $C_{10}$-$C_{30}$ alkyl acrylate (hydrophobic unit) and 0.1% to 0.6% by weight of crosslinking polymerizable monomer; or (ii) acrylic acid and lauryl methacrylate, such as the polymers formed from 66% by weight of acrylic acid and 34% by weight of lauryl methacrylate.

The crosslinking agent can be a monomer comprising a group

with at least one other polymerizable group whose unsaturated bonds are not conjugated with respect to one another. Mention may be made, for example, of polyallyl ethers such as polyallylsucrose and polyallylpentaerythritol.

Among said polymers above mention may be made, for example, of the products sold by the company Goodrich under the trade names Pemulen TR1, Pemulen TR2, Carbopol 1382, and further, for example, Pemulen TR1, and the product sold by the company S.E.P.C. under the name Coatex SX.

Among anionic amphiphilic fatty-chain polymers, mention may also be made, for example, of the methacrylic acid/methyl acrylate/ethoxylated alkyl dimethyl-meta-isopropenylbenzylisocyanate copolymer sold under the name Viscophobe DB 1000 by the company Amerchol.

The cationic amphiphilic polymers used are, for example, chosen from quaternized cellulose derivatives and polyacrylates comprising amino side groups.

The quaternized cellulose derivatives are, for example, chosen from
    quaternized celluloses modified with groups comprising at least one fatty chain, such as alkyl, arylalkyl and alkylaryl groups comprising at least 8 carbon atoms, and mixtures thereof,
    quaternized hydroxyethylcelluloses modified with groups comprising at least one fatty chain, such as alkyl, arylalkyl and alkylaryl groups comprising at least 8 carbon atoms, and mixtures thereof.

Quaternized and non-quaternized polyacrylates comprising amino side groups having for example, hydrophobic groups, such as Steareth 20 (polyoxy-ethylenated(20) stearyl alcohol) and ($C_{10}$-$C_{30}$)alkyl PEG-20 itaconate.

The alkyl radicals borne by the above quaternized celluloses and hydroxyethylcelluloses, for example, contain from 8 to 30 carbon atoms.

The aryl radicals, for example, are chosen from phenyl, benzyl, naphthyl and anthryl groups.

Examples of quaternized alkylhydroxyethyl-celluloses comprising $C_8$-$C_{30}$ fatty chains are the products Quatrisoft LM 200, Quatrisoft LM-X 529-18-A, Quatrisoft LM-X 529-18B ($C_{12}$ alkyl) and Quatrisoft LM-X 529-8 ($C_{18}$ alkyl) sold by the company Amerchol, and the products Crodacel QM, Crodacel QL ($C_{12}$ alkyl) and Crodacel QS ($C_{18}$ alkyl) sold by the company Croda.

Examples of polyacrylates comprising amino side chains are the polymers 8781-124B or 9492-103 and Structure Plus from the company National Starch.

Among amphoteric amphiphilic polymers comprising at least one hydrophilic unit and at least one fatty-chain unit, mention may be made, for example, of methacrylamidopropyltrimethylammonium chloride/acrylic acid/$C_{10}$-$C_{30}$ alkyl methacrylate copolymers, wherein the alkyl radical is, for example, a stearyl radical.

The associative thickeners in the cosmetic compositions can have, for example, in solution or in dispersion at a concentration of 1% active material in water, a viscosity, measured using a Rheomat RM 180 rheometer at 25° C., of greater than 0.1 ps and further, for example, of greater than 0.2 cp, at a shear rate of 200 $s^{-1}$.

(ii) Among the crosslinked acrylic acid homopolymers that may be mentioned are those crosslinked with an allylic alcohol ether of the sugar series, such as the products sold under the names Carbopol 980, 981, 954, 2984 and 5984 by the company Goodrich or the products sold under the names Synthalen M and Synthalen K by the company 3 VSA.

(iii) Crosslinked copolymers of (meth)acrylic acid and of $C_1$-$C_6$ alkyl acrylate can be chosen from crosslinked copolymers of methacrylic acid and of ethyl acrylate as an aqueous dispersion comprising 38% active material sold, for example, under the name Viscoatex 538C by the company Coatex, and crosslinked copolymers of acrylic acid and of ethyl acrylate as an aqueous dispersion comprising 28% active material sold under the name Aculyn 33 by the company Rohm & Haas. Crosslinked copolymers of methacrylic acid and of ethyl acrylate include an aqueous dispersion comprising 30% active material manufactured and sold under the name Carbopol Aqua SF-1 by the company Noveon.

(iv) Among the nonionic homopolymers or copolymers comprising ethylenically unsaturated monomers of ester and/or amide type, mention may be made of the products sold under the names: Cyanamer P250 by the company Cytec (polyacrylamide); PMMA MBX-8C by the company US Cosmetics (methyl methacrylate/ethylene glycol dimethacrylate copolymer); Acryloid B66 by the company Rohm & Haas (butyl methacrylate/methyl methacrylate copolymer); BPA 500 by the company Kobo (polymethyl methacrylate).

(v) Ammonium acrylate homopolymers that may be mentioned include the product sold under the name Microsap PAS 5193 by the company Hoechst.

Copolymers of ammonium acrylate and of acrylamide include the product sold under the name Bozepol C Nouveau or the product PAS 5193 sold by the company Hoechst (which are described and prepared in documents FR-2 416 723, U.S. Pat. Nos. 2,798,053 and 2,923,692).

(vi) The polysaccharides are, for example, chosen from glucans, modified and unmodified starches (such as those derived, for example, from cereals, for instance wheat, corn or rice, from vegetables, for instance yellow pea, and tubers, for instance potato or cassava), amylose, amylopectin, glycogen, dextrans, celluloses and derivatives thereof (methylcelluloses, hydroxyalkylcelluloses, ethylhydroxyethylcelluloses, and carboxymethylcelluloses), mannans, xylans, lignins, arabans, galactans, galacturonans, chitin, chitosans, glucuronoxylans, arabinoxylans, xyloglucans, glucomannans, pectic acids and pectins, alginic acid and alginates, arabinogalactans, carrageenans, agars, glycosaminoglucans, gum arabics, gum tragacanths, ghatti gums, karaya gums, carob gums, galactomannans, such as guar gums, and nonionic derivatives thereof (hydroxypropyl guar) and xanthan gums, and mixtures thereof.

For example, the polysaccharides that may be used are chosen from those described, for example, in "Encyclopedia of Chemical Technology", Kirk-Othmer, Third Edition, 1982, volume 3, pp. 896-900, and volume 15, pp. 439-458, in "Polymers in Nature" by E. A. MacGregor and C. T. Greenwood, published by John Wiley & Sons, Chapter 6, pp. 240-328, 1980, and in "Industrial Gums—Polysaccharides and their Derivatives", edited by Roy L. Whistler, Second Edition, published by Academic Press Inc., the content of these three publications being entirely incorporated by reference.

For example, starches, guar gums and celluloses and derivatives thereof can be used.

Among the starches that may be used, mention may be made, for example, of macromolecules in the form of polymers comprising elemental moieties that are anhydroglucose units. The number of these moieties and their assembly make it possible to distinguish between amylose (linear polymer) and amylopectin (branched polymer). The relative proportions of amylose and of amylopectin, and also their degree of polymerization, can vary as a function of the botanical origin of the starches.

The botanical origin of the starch molecules used may be cereals or tubers. Thus, the starches can be, for example, chosen from corn starch, rice starch, cassava starch, tapioca starch, barley starch, potato starch, wheat starch, sorghum starch and pea starch.

Starches are generally in the form of a white powder, which is insoluble in cold water and which has an elementary particle size ranging from 3 to 100 microns.

The starches may optionally be C1-C6 hydroxyalkylated or C1-C6 acylated (such as acetylated). The starches may also have undergone heat treatments.

Distarch phosphates or of compounds rich in distarch phosphate, for instance the products sold under the references Prejel VA-70-T AGGL (gelatinized hydroxypropylated cassava distarch phosphate) or Prejel TK1 (gelatinized cassava distarch phosphate) or Prejel 200 (gelatinized acetylated cassava distarch phosphate) by the company Avebe, or Structure ZEA from National Starch (hydroxypropylated corn distarch phosphate), may also be used.

The guar gums may be modified or unmodified.

The unmodified guar gums are, for example, the products sold under the name Vidogum GH 175 by the company Unipectine and under the names Meyro-Guar 50 and Jaguar C by the company Meyhall.

The modified nonionic guar gums are, for example, modified with $C_1$-$C_6$ hydroxyalkyl groups.

Among hydroxyalkyl groups, mention may be made, for example, of hydroxymethyl, hydroxyethyl, hydroxypropyl and hydroxybutyl groups.

These guar gums are well known in the state of the art and can be prepared, for example, by reacting corresponding alkene oxides, such aspropylene oxides, with guar gum so as to obtain a guar gum modified with hydroxypropyl groups.

The degree of hydroxyalkylation, which corresponds to the number of alkylene oxide molecules consumed by the number of free hydroxyl functions present on the guar gum, may, for example, range from 0.4 to 1.2.

Such nonionic guar gums optionally modified with hydroxyalkyl groups are sold, for example, under the trade names Jaguar HP8, Jaguar HP60 and Jaguar HP120, Jaguar DC 293 and Jaguar HP 105 by the company Rhodia Chimie (Meyhall) or under the name Galactasol 4H4FD2 by the company Aqualon.

Among the celluloses that are used are, for example, hydroxyethylcellulose and hydroxypropylcelluloses. Mention may be made of the products sold under the names Klucel E F, Klucel H, Klucel L H F, Klucel M F and Klucel G by the company Aqualon.

(vii) The fatty alcohols are, for example, chosen from myristyl alcohol, cetyl alcohol, stearyl alcohol and behenyl alcohol.

The at least one thickener may represent an amount ranging, for example, from 0.001% to 20% by weight, and further, for example, from 0.01% to 10% by weight and even further, for example, from 0.1% to 3% by weight, relative to the total weight of the composition.

In one embodiment, the composition further comprises at least one cationic polymer.

The cationic polymers that may be used may be chosen from any of those already known per se as improving the cosmetic properties of hair treated with detergent compositions, for example, those described in patent application EP-A-0 337 354 and in French patent applications FR-A-2 270 846, 2 383 660, 2 598 611, 2 470 596 and 2 519 863.

The cationic polymers can be chosen, for example, from those comprising units comprising at least one amine group chosen from primary, secondary, tertiary and quaternary amine groups that may either form part of the main polymer chain, or be borne by a side substituent that is directly attached to the main polymer chain.

The cationic polymers used generally have a number-average molar mass ranging, for example, from 500 to $5 \times 10^6$ approximately and further, for example, from $10^3$ to $3 \times 10^6$ approximately.

Among the cationic polymers that may be mentioned, for example, are polymers of the polyamine, polymers of polyamino amide and polymers of polyquaternary ammonium. These polymers are known in the art.

Polymers of polyamine, polymers of polyamino amide and polymers of polyquaternary ammonium that may be used, for example, are described in French Patent Nos. 2 505 348 and 2 542 997. Among these polymers, mention may be made of:

(1)homopolymers and copolymers derived from acrylic or methacrylic esters or amides and comprising at least one of the units of the following formulae:

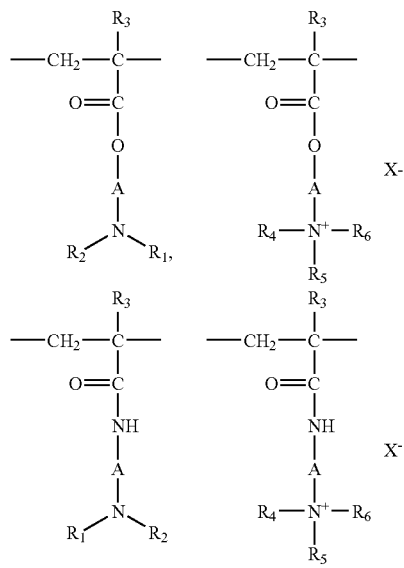

in which:

$R_1$ and $R_2$, which may be identical or different, are chosen from a hydrogen atom and alkyl groups comprising from 1 to 6 carbon atoms, for example, methyl and ethyl groups;

$R_3$, which may be identical or different, is chosen from a hydrogen atom and a $CH_3$ radical;

A, which may be identical or different, is chosen from linear and branched alkyl groups of 1 to 6 carbon atoms, such as 2 or 3 carbon atoms, and hydroxyalkyl groups of 1 to 4 carbon atoms;

$R_4$, $R_5$ and $R_6$, which may be identical or different, are chosen from alkyl groups comprising from 1 to 18 carbon atoms and benzyl radicals such as alkyl groups comprising from 1 to 6 carbon atoms;

$X^-$ is an anion derived from a mineral or organic acid, such as a methosulphate anion or an anion chosen from halides such as chloride or bromide.

Copolymers of family (1) can also comprise at least one unit derived from comonomers, which may be chosen from the family of acrylamides, methacrylamides, diacetone acrylamides, acrylamides and methacrylamides substituted on the nitrogen with lower ($C_1$-$C_4$) alkyls, acrylic acids, methacrylic acids, acrylic esters, methacrylic esters, vinyllactams such as vinylpyrrolidone and vinylcaprolactam, and vinyl esters.

Thus, among these copolymers of family (1), mention may be made of:

the copolymers of acrylamide and of dimethylaminoethyl methacrylate quaternized with dimethyl sulphate or with a dimethyl halide, such as the product sold under the name Hercofloc by the company Hercules, the copolymers of acrylamide and of methacryloyloxyethyltrimethylammonium chloride described, for example, in patent application EP-A-080 976 and sold under the name Bina Quat P 100 by the company Ciba, the copolymer of acrylamide and of methacryloyloxyethyltrimethylammonium methosulphate sold under the name Reten by the company Hercules, quaternized or non-quaternized vinylpyrrolidone/dialkylaminoalkyl acrylate or methacrylate copolymers, such as the products sold under the name "Gafquat" by the company ISP, such as "Gafquat® 734" or "Gafquat® 755", or alternatively the products known as "Copolymer 845, 958 and 937". These polymers are described in detail in French Patent Nos. 2 077 143 and 2 393 573, dimethylaminoethyl methacrylate/vinylcaprolactam/vinylpyrrolidone terpolymers, such as the product sold under the name Gaffix® VC 713 by the company ISP, vinylpyrrolidone/methacrylamidopropyldimethylamine copolymers sold, for example, under the name Styleze® CC 10 by ISP, and quaternized vinylpyrrolidone/dimethylaminopropylmethacrylamide copolymers such as the product sold under the name "Gafquat® HS 100" by the company ISP.

(2)cationic polysaccharides, such as cationic celluloses and cationic galactomannan gums. Among the cationic polysaccharides that may be mentioned for example, are cellulose ether derivatives comprising quaternary ammonium groups, cationic cellulose copolymers or cellulose derivatives grafted with a water-soluble quaternary ammonium monomer and cationic galactomannan gums.

The cellulose ether derivatives comprising quaternary ammonium groups, which are described in French Patent No.1 492 597, are, for example, the polymers sold under the names "JR" (JR 400, JR 125, JR 30M) or "LR" (LR 400, LR 30M) by the company Amerchol. These polymers are also defined in the CTFA dictionary as hydroxyethylcellulose quaternary ammoniums that have reacted with an epoxide substituted with a trimethylammonium group.

The cationic cellulose copolymers or cellulose derivatives grafted with a water-soluble quaternary ammonium monomer are described, for example, in U.S. Pat. No. 4,131,576, such as hydroxyalkylcelluloses, for instance hydroxymethyl-, hydroxyethyl- or hydroxypropylcelluloses grafted, for example, with a salt chosen from methacryloyl-ethyltrimethylammonium, methacrylamidopropyltrimethylammonium and dimethyldiallylammonium salts.

The commercial products corresponding to this definition are, for example, the products sold under the name "Celquat® L 200" and "Celquat® H 100" by the company National Starch.

The cationic galactomannan gums are described, for example, in U.S. Pat. Nos. 3,589,578 and 4,031,307, such as guar gums comprising trialkylammonium cationic groups. For example, guar gums modified with a salt (e.g. chloride) of 2,3-epoxypropyltrimethylammonium may be used.

Such polymers are sold, for example, under the trade names Jaguar® C13S, Jaguar) C15, Jaguar® C17 and Jaguar® C162 by the company Meyhall.

(3)polymers comprising piperazinyl units and divalent alkylene or hydroxyalkylene radicals comprising straight or branched chains, optionally interrupted with at least one atom chosen from oxygen, sulphur and nitrogen or with at least one ring chosen from aromatic and heterocyclic rings, and at least one of the oxidation and/or quaternization products of these polymers. Such polymers are described, for example, in French Patent Nos. 2 162 025 and 2 280 361;

(4) water-soluble polyamino amides prepared, for example, by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative. The crosslinking agent can be used in proportions ranging from 0.025 to 0.35 mol per amine group of the polyamino amide. These polyamino amides can be alkylated or, if they comprise at least one tertiary amine function, they can be quaternized. Such polymers are described, for example, in French Patent Nos. 2 252 840 and 2 368 508;

(5) polyamino amide derivatives resulting from the condensation of polyalkylene polyamines with polycarboxylic acids followed by alkylation with difunctional agents. Mention may be made, for example, of adipic acid/dialkylaminohydroxyalkyldialkylenetriamine polymers in which the alkyl radical comprises from 1 to 4 carbon atoms, such as methyl, ethyl and propyl. Such polymers are described, for example, in French Patent No. 1 583 363.

Among these derivatives, mention may be made, for example, of the adipic acid/dimethylaminohydroxypropyl/diethylenetriamine polymers sold under the name "Cartaretine® F, F4 or F8" by the company Sandoz.

(6) polymers obtained by reaction of a polyalkylene polyamine comprising two primary amine groups and at least one secondary amine group with a dicarboxylic acid chosen from diglycolic acids and saturated aliphatic dicarboxylic acids comprising from 3 to 8 carbon atoms. The molar ratio between the polyalkylene polyamine and the dicarboxylic acid may range, for example, from 0.8:1 to 1.4:1; the polyamino amide resulting therefrom may be reacted with epichlorohydrin in a molar ratio of epichlorohydrin relative to the secondary amine group of the polyamino amide ranging, for example, from 0.5:1 to 1.8:1. Such polymers are described, for example, in U.S. Pat. Nos. 3,227,615 and 2,961,347.

Other non-limiting examples of such derivatives include the adipic acid/epoxypropyl/diethylenetriamine copolymer sold, for example, under the name "Hercosett® 57" by the company Hercules Inc. or under the name "PD 170" or "Delsette® 101" by the company Hercules.

(7) cyclopolymers of alkyldiallylamine or of dialkyldiallylammonium, such as the homopolymers or copolymers comprising, as main constituent of the chain, at least one unit corresponding to formula (VII) or (VIII):

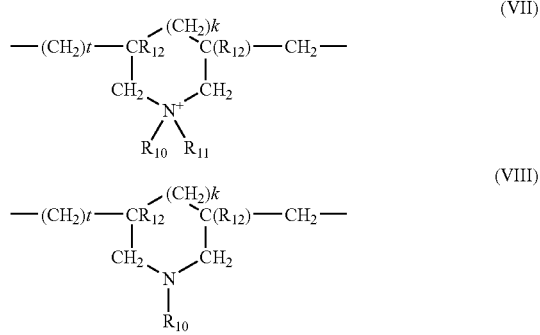

in which k and t are equal to 0 or 1, the sum k+t being equal to 1;

$R_{12}$ is chosen from a hydrogen atom and a methyl radical;

$R_{10}$ and $R_{11}$, which may be identical or different, are chosen from alkyl groups comprising from 1 to 8 carbon atoms, hydroxyalkyl groups in which the alkyl group, for example, comprises from 1 to 5 carbon atoms, and lower ($C_1$-$C_4$) amidoalkyl groups, or $R_{10}$ and $R_{11}$, are chosen from, together with the nitrogen atom to which they are attached, heterocyclic groups such as piperidyl or morpholinyl; $Y^-$ is an anion such as bromide, chloride, acetate, borate, citrate, tartrate, bisulphate, bisulphite, sulphate and phosphate. These polymers are described, for example, in French Patent No. 2 080 759 and in its Certificate of Addition 2 190 406.

In one embodiment, $R_{10}$ and $R_{11}$, which may be identical or different, are, for example, chosen from alkyl groups comprising from 1 to 4 carbon atoms.

Among the polymers defined above, mention may be made, for example, of the dimethyldiallylammonium chloride homopolymer sold under the name "Merquat® 100" by the company Nalco (and its homologues of low weight-average molecular mass) and copolymers of diallyldimethylammonium chloride and of acrylamide, sold under the name "Merquat® 550".

(8) quaternary diammonium polymers comprising repeating units corresponding to the formula (IX):

in which $R_{13}$, $R_{14}$, $R_{15}$ and $R_{16}$, which may be identical or different, are chosen from aliphatic, alicyclic and arylaliphatic radicals comprising from 1 to 20 carbon atoms and from lower hydroxyalkylaliphatic radicals, or $R_{13}$, $R_{14}$, $R_{15}$ and $R_{16}$, together or separately, constitute, with the nitrogen atoms to which they are attached, heterocycles optionally comprising a second hetero atom other than nitrogen, or $R_{13}$, $R_{14}$, $R_{15}$ and $R_{16}$ are chosen from linear and branched $C_1$-$C_6$ alkyl radicals substituted with at least one group chosen from nitrile, ester, acyl and amide groups and groups of —CO—O—$R_{17}$-D and —CO—NH—$R_{17}$-D wherein $R_{17}$ is chosen from alkylene groups and D is chosen from quaternary ammonium groups;

$A_1$ and $B_1$ which may be identical or different, are chosen from linear and branched, saturated and unsaturated polymethylene groups comprising from 2 to 20 carbon atoms. The polymethylene groups may comprise, linked to or intercalated in the main chain, at least one entity chosen from aromatic rings, oxygen, and sulphur atoms and sulphoxide, sulphone, disulphide, amino, alkylamino, hydroxyl, quaternary ammonium, ureido, amide and ester groups, and $X^-$ is an anion chosen from anions derived from mineral acids and organic acids;

$A_1$, $R_{13}$ and $R_{15}$ may optionally form, with the two nitrogen atoms to which they are attached, a piperazine ring; in addition, if $A_1$ is a radical chosen from linear and branched, saturated and unsaturated alkylene and hydroxyalkylene radicals, $B_1$ can also represent a group $(CH_2)_n$—CO-D-OC—$(CH_2)_n$—, wherein n ranges from 1 to 100, such as from 1 to 50.

D is chosen from:

a) a glycol residue of formula: —O—Z—O—, wherein Z is chosen from linear and branched hydrocarbon-based radicals and a group corresponding to one of the following formulae:

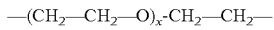
—(CH$_2$—CH$_2$—O)$_x$-CH$_2$—CH$_2$—

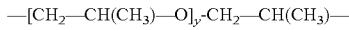
—[CH$_2$—CH(CH$_3$)—O]$_y$-CH$_2$—CH(CH$_3$)— wherein x and y, which may be identical or different, are each an integer ranging from 1 to 4, representing a defined and unique degree of polymerization or any number from 1 to 4 representing an average degree of polymerization;

b) a bis-secondary diamine residue such as a piperazine derivative;

c) a bis-primary diamine residue of formula: —NH—Y—NH—, wherein Y is chosen from linear and branched hydrocarbon-based radicals, and the divalent radical

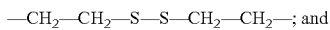
—CH$_2$—CH$_2$—S—S—CH$_2$—CH$_2$—; and d) a ureylene group of formula: —NH—CO—NH—.

For example, X$^-$ is an anion such as chloride or bromide.

These polymers may have a number-average molecular mass ranging from 1000 to 100 000.

These polymers are described, for example, in French Patent Nos. 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

Further, polymers can comprise repeating units corresponding to the formula (X):

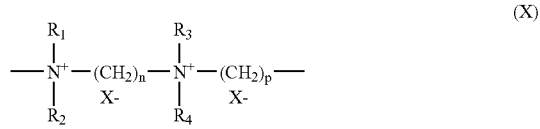

(X)

in which $R_1$, $R_2$, $R_3$ and $R_4$, which may be identical or different, are chosen from alkyl and hydroxyalkyl radicals comprising from 1 to 4 carbon atoms, n and p, which are identical or different, are integers ranging from 2 to 20, and X$^-$ is an anion chosen from anions derived from mineral acids and organic acids.

One compound of formula (X), for example, is the one for which $R_1$, $R_2$, $R_3$ and $R_4$ are each a methyl radical and n=3, p=6 and X=Cl, which is known as Hexadimethrine chloride according to the INCI (CTFA) nomenclature.

(9) polyquaternary ammonium polymers comprising repeating units of formula (XI):

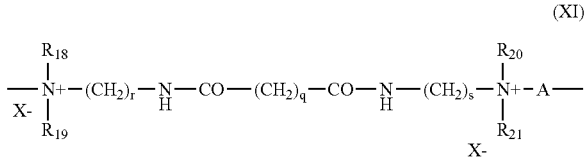

(XI)

in which:

$R_{18}$, $R_{19}$, $R_{20}$ and $R_{21}$, which may be identical or different, are chosen from a hydrogen atom and methyl, ethyl, propyl, β-hydroxyethyl, β-hydroxypropyl and —CH$_2$CH$_2$(OCH$_2$CH$_2$)$_p$OH radicals, wherein p is equal to 0 or to an integer ranging from 1 to 6, with the proviso that $R_{18}$, $R_{19}$, $R_{20}$ and $R_{21}$ do not simultaneously represent a hydrogen atom, r and s, which may be identical or different, are each an integer ranging from 1 to 6, q is equal to 0 or to an integer ranging from 1 to 34, X$^-$ is an anion such as a halide, A is chosen from divalent radicals, such as —CH$_2$—CH$_2$—O—CH$_2$—CH$_2$—.

Such polymers are described, for example, in patent application EP-A-122 324.

Among these polymers, mention may be made, for example, of "Mirapol® A 15", "Mirapol® AD1", "Mirapol® AZ1" and "Mirapol® 175" sold by the company Miranol.

(10) quaternary polymers of vinylpyrrolidone and of vinylimidazole, such as the products sold under the names Luviquat® FC 905, FC 550 and FC 370 by the company BASF.

(11) polyamines such as the product Polyquart® H sold by Cognis under the reference name "Polyethylene Glycol (15) Tallow Polyamine" in the CTFA dictionary.

(1.2) crosslinked methacryloyloxy($C_1$-$C_4$)alkyltri($C_1$-$C_4$) alkylammonium salt polymers such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound comprising olefinic unsaturation, such as methylenebisacrylamide. In one embodiment, a crosslinked acrylamide/methacryloyloxyethyltrimethylammonium chloride copolymer (20/80 by weight) in the form of a dispersion comprising 50% by weight of the said copolymer in mineral oil may be used. This dispersion is sold under the name "Salcare® SC 92" by the company Ciba. In another embodiment, a crosslinked homopolymer of methacryloyloxyethyltrimethylammonium chloride comprising about 50% by weight of the homo-polymer in mineral oil or in a liquid ester may be used. These dispersions are sold under the names "Salcare® SC 95" and "Salcare® SC 96" by the company Ciba.

Other cationic polymers which can be used are chosen from cationic proteins and cationic protein hydrolysates, polyalkyleneimines, such as polyethyleneimines, polymers comprising units chosen from vinylpyridine and vinylpyridinium units, condensates of polyamines and of epichlorohydrin, quaternary polyureylenes and chitin derivatives.

Among all the cationic polymers that may be used, non-limiting examples include quaternary cellulose ether derivatives such as the products sold under the name "JR 400" by the company Amerchol, cationic cyclopolymers, such as the dimethyldiallylammonium chloride homopolymers or copolymers sold under the names "Merquat® 100", "Merquat® 550" and "Merquat® S" by the company Nalco, quaternary polymers of vinylpyrrolidone and of vinylimidazole, and mixtures thereof.

The at least one polymer chosen from cationic polymers may be present in an amount ranging, for example, from 0.001% to 20% by weight, such as from 0.01% to 10% by weight and further such as from 0.1% to 3% by weight, relative to the total weight of the composition.

The compositions can also comprise at least one surfactant, which is generally present in an amount ranging, for example, from 0.1% to 60% by weight such as from 3% to 40% by weight and further such as from 5% to 30% by weight relative to the total weight of the composition.

This at least one surfactant may be chosen from anionic, amphoteric, nonionic and cationic surfactants.

The at least one surfactant that is suitable is, for example, chosen from:

(i) Anionic Surfactants:

As examples of anionic surfactants, which can be used, alone or as mixtures, mention may be made, for example, of salts (such as alkaline salts, for example, sodium salts, ammonium salts, amine salts, amino alcohol salts and magnesium salts) of the following compounds: alkyl sulphates, alkyl ether sulphates, alkylamido ether sulphates, alkylarylpolyether sulphates, monoglyceride sulphates; alkyl sulphonates, alkyl phosphates, alkylamide sulphonates, alkylaryl sulphonates, α-olefin sulphonates, paraffin sulphonates; alkyl sulphosuccinates, alkyl ether sulphosuccinates, alkylamide sulphosuccinates; alkyl sulphosuccinamates; alkyl sulphoacetates; alkyl ether phosphates; acyl sarcosinates; acyl isethionates and N-acyltaurates. The alkyl or acyl radical of all of these various compounds, for example, comprises from 8 to 24 carbon atoms, and the aryl radical, for example, is chosen from phenyl and benzyl groups. Among the anionic surfactants, which can also be used, mention may also be made of fatty acid salts such as the salts of oleic, ricinoleic, palmitic and stearic acids, coconut oil acid or hydrogenated coconut oil acid; acyl lactylates in which the acyl radical comprises from 8 to 20 carbon atoms. Weakly anionic surfactants can also be used, such as alkyl-D-galactosiduronic acids and their salts, as well as polyoxyalkylenated ($C_6$-$C_{24}$) alkyl ether carboxylic acids, polyoxyalkylenated ($C_6$-$C_{24}$) alkylaryl ether carboxylic acids, polyoxyalkylenated ($C_6$-$C_{24}$) alkylamido ether carboxylic acids and their salts, for example, those comprising from 2 to 50 ethylene oxide groups, and mixtures thereof.

Among the anionic surfactants, for example, alkyl sulphate salts and alkyl ether sulphate salts and mixtures thereof can be used.

(ii) Nonionic Surfactants:

The nonionic surfactants are compounds that are well known (see, for example, in this respect "Handbook of Surfactants" by M. R. Porter, published by Blackie & Son (Glasgow and London), 1991, pp. 116-178). They can be chosen, for example, from polyethoxylated, polypropoxylated and polyglycerolated fatty acids, alkylphenols, α-diols and alcohols comprising a fatty chain comprising, for example, from 8 to 18 carbon atoms, it being possible for the number of ethylene oxide or propylene oxide groups to range, for example, from 2 to 50 and for the number of glycerol groups to range, for example, from 2 to 30. Mention may also be made of copolymers of ethylene oxide and of propylene oxide, condensates of ethylene oxide and of propylene oxide with fatty alcohols; polyethoxylated fatty amides preferably having from 2 to 30 mol of ethylene oxide, polyglycerolated fatty amides, for example, comprising on average from 1 to 5, and such as from 1.5 to 4, glycerol groups; polyethoxylated fatty amines such as those containing from 2 to 30 mol of ethylene oxide; oxyethylenated fatty acid esters of sorbitan having from 2 to 30 mol of ethylene oxide; fatty acid esters of sucrose, fatty acid esters of polyethylene glycol, alkylpolyglycosides, N-alkylglucamine derivatives, amine oxides such as ($C_{10}$-$C_{14}$)alkylamine oxides or N-acylaminopropylmorpholine oxides. It may be noted that the alkylpolyglycosides constitute nonionic surfactants that can be used.

(iii) Amphoteric Surfactants:

The amphoteric surfactants can be chosen, for example, from aliphatic secondary and tertiary amine derivatives in which the aliphatic radical is chosen from linear and branched chains comprising from 8 to 22 carbon atoms and comprising at least one water-soluble anionic group (for example carboxylate, sulphonate, sulphate, phosphate or phosphonate); mention may also be made of ($C_8$-$C_{20}$)alkylbetaines, sulphobetaines, ($C_8$-$C_{20}$)alkylamido($C_1$-$C_6$)alkylbetaines or ($C_8$-$C_{20}$)alkylamido($C_1$-$C_6$)alkylsulphobetaines.

Among the amine derivatives, mention may be made of the products sold under the name Miranol, as described, for example, in U.S. Pat. Nos. 2,528,378 and 2,781,354 and having the structures of:

$$R_2—CONHCH_2CH_2—N^+(R_3)(R_4)(CH_2COO^-) \quad (2)$$

in which: $R_2$ is chosen from alkyl radicals derived from an acid $R_2$—COOH present in hydrolysed coconut oil, and heptyl, nonyl and undecyl radicals, $R_3$ is a β-hydroxyethyl group and $R_4$ is a carboxymethyl group;

and of $$R_5—CONHCH_2CH_2—N(B)(C) \quad (3)$$

wherein B represents —$CH_2CH_2OX'$, C represents —$(CH_2)_z$-Y', with z=1 or 2, X' is chosen from the —$CH_2CH_2$—COOH group and a hydrogen atom, Y' is chosen from —COOH and —$CH_2$—CHOH—$SO_3H$ radicals, $R_5$ is chosen from alkyl radicals of an acid $R_5$—COOH present in coconut oil or in hydrolysed linseed oil, alkyl radicals, such as $C_7$, $C_9$, $C_{11}$ and $C_{13}$ alkyl radicals, a $C_{17}$ alkyl radical and its iso form, and unsaturated $C_{17}$ radical.

These compounds are classified in the CTFA dictionary, 5th edition, 1993, under the names disodium cocoamphodiacetate, disodium lauroamphodiacetate, disodium caprylamphodiacetate, disodium caprylamphodiacetate, disodium cocoamphodipropionate, disodium lauroamphodipropionate, disodium caprylampho-dipropionate, disodium caryloamphodipropionate, lauroamphodipropionic acid, and cocoamphodipropionic acid.

By way of example, mention may be made of the cocoamphodiacetate sold under the trade name Miranol C2M concentrate by the company Rhodia Chimie.

(iv) Cationic Surfactants:

The cationic surfactants may be chosen from:

A) the quaternary ammonium salts of general formula (XII) below:

$$\begin{bmatrix} R_1 & R_3 \\ \diagdown N \diagup & \\ R_2 & R_4 \end{bmatrix}^+ X^- \quad (XII)$$

wherein $X^-$ is an anion chosen from halides (chloride, bromide and iodide), ($C_2$-$C_6$)alkyl sulphates, such as methyl sulphate, phosphates, alkyl and alkylaryl sulphonates, and anions derived from organic acids, such as acetate and lactate, and i) the radicals $R_1$ to $R_3$, which may be identical or different, are chosen from linear and branched aliphatic radicals comprising from 1 to 4 carbon atoms, and aromatic radicals such as aryl and alkylaryl. The aliphatic radicals can comprise at least one hetero atom such as oxygen, nitrogen, sulphur and halogens. The aliphatic radicals are chosen, for example, from alkyl, alkoxy and alkylamide radicals, $R_4$ is chosen from linear and branched alkyl radicals comprising from 16 to 30 carbon atoms.

The cationic surfactant is, for example, a behenyltrimethylammonium salt (for example chloride).

ii) the radicals $R_1$ and $R_2$, which may be identical or different, are chosen from linear and branched aliphatic radicals comprising from 1 to 4 carbon atoms, and aromatic radicals such as aryl and alkylaryl. The aliphatic radicals can comprise at least one hetero atom such as oxygen, nitrogen, sulphur and halogens. The aliphatic radicals are chosen, for example, from alkyl, alkoxy, alkylamide and hydroxyalkyl radicals comprising from about 1 to 4 carbon atoms;

$R_3$ and $R_4$, which may be identical or different, are chosen from linear and branched alkyl radicals comprising from 12 to 30 carbon atoms, the said alkyl radicals comprise at least one function chosen from ester and amide functions.

$R_3$ and $R_4$ are chosen, for example, from $(C_{12}-C_{22})$alkylamido$(C_2-C_6)$alkyl and $(C_{12}-C_{22})$alkylacetate radicals.

The cationic surfactant is, for example, a stearamidopropyldimethyl(myristyl acetate)ammonium salt (for example chloride);

B)—the quaternary ammonium salts of imidazolinium, such as that of formula (XIII) below:

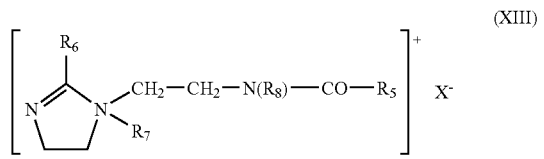

in which $R_5$ is chosen from alkenyl and alkyl radicals comprising from 8 to 30 carbon atoms, for example fatty acid derivatives of tallow, $R_6$ is chosen from a hydrogen atom, $C_1-C_4$ alkyl radicals and alkenyl and alkyl radicals comprising from 8 to 30 carbon atoms, $R_7$ is chosen from $C_1-C_4$ alkyl radicals, $R_8$ is chosen from a hydrogen atom and $C_1-C_4$ alkyl radicals, and $X^-$ is an anion chosen from halides, phosphates, acetates, lactates, alkyl sulphates, alkyl sulphonates and alkylaryl sulphonates.

In one embodiment, $R_5$ and $R_6$ are, for example, a mixture of radicals chosen from alkenyl and alkyl radicals comprising from 12 to 21 carbon atoms, such as fatty acid derivatives of tallow, $R_7$ is methyl and $R_8$ is hydrogen. Such a product is, for example, Quaternium-27 (CTFA 1997) or Quaternium-83 (CTFA 1997), which are sold under the names "Rewoquat®" W75, W90, W75PG and W75HPG by the company Witco, C)—the diquaternary ammonium salts of formula (XIV):

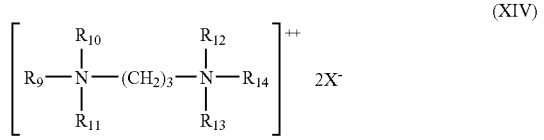

in which $R_9$ is chosen from aliphatic radicals comprising from about 16 to 30 carbon atoms, $R_{10}$, $R_{11}$, $R_{12}$, $R_{13}$ and $R_{14}$, which may be identical or different, are chosen from hydrogen and alkyl radicals comprising from 1 to 4 carbon atoms, and $X^-$ is an anion chosen from halides, acetates, phosphates, nitrates and methyl sulphates. Such diquaternary ammonium salts, for example, include propanetallowdiammmonium dichloride; and D)—the quaternary ammonium salts comprising at least one ester function, of formula (XV) below:

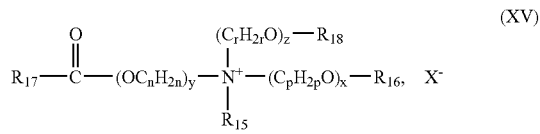

in which:

$R_{15}$ is chosen from $C_1-C_6$ alkyl radicals and $C_1-C_6$ hydroxyalkyl and dihydroxyalkyl radicals;

$R_{16}$ is chosen from:

a radical

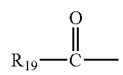

linear and branched, saturated and unsaturated $C_1-C_{22}$ hydrocarbon-based radicals $R_{20}$, and a hydrogen atom, $R_{18}$ is chosen from:

a radical

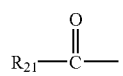

linear and branched, saturated and unsaturated $C_1-C_6$ hydrocarbon-based radicals $R_{22}$, and a hydrogen atom, $R_{17}$, $R_{19}$ and $R_{21}$, which may be identical or different, are chosen from linear and branched, saturated and unsaturated $C_7-C_{21}$ hydrocarbon-based radicals;

n, p and r, which may be identical or different, are chosen from integers ranging from 2 to 6;

y is chosen from integers ranging from 1 to 10;

x and z, which may be identical or different, are chosen from integers ranging from 0 to 10;

$X^-$ is an anion chosen from simple and complex, organic and inorganic anions;

with the proviso that the sum x+y+z is from 1 to 15, that when x is 0, then $R_{16}$ is $R_{20}$ and that when z is 0, then $R_{18}$ is $R_{22}$.

In one embodiment, the ammonium salts of formula (XV) can be used, in which:

$R_{15}$ is chosen from methyl and ethyl radicals, x and y are equal to 1;

z is equal to 0 or 1;

n, p and r are equal to 2;

$R_{16}$ is chosen from:

a radical

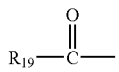

methyl, ethyl and $C_{14}$-$C_{22}$ hydrocarbon-based radicals, and a hydrogen atom;

$R_{17}$, $R_{19}$ and $R_{21}$, which may be identical or different, are chosen from linear and branched, saturated and unsaturated $C_7$-$C_{21}$ hydrocarbon-based radicals;

$R_{18}$ is chosen from:

a radical

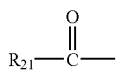

and a hydrogen atom.

Such compounds are sold, for example, under the names Dehyquart by the company Cognis, Stepanquat by the company Stepan, Noxamium by the company Ceca, and Rewoquat WE 18 by the company Rewo-Witco.

Among the quaternary ammonium salts, examples are behenyltrimethylammonium chloride and also stearamidopropyldimethyl(myristyl acetate)ammonium chloride, sold under the name "Ceraphyl 70" by the company Van Dyk, and Quaternium-27 or Quaternium-83 sold by the company Witco.

Among the anionic surfactants, examples are sodium, triethanolamine and ammonium ($C_{12}$-$C_{14}$)alkyl sulphates, sodium, triethanolamine and ammonium ($C_{12}$-$C_{14}$)alkyl ether sulphates oxyethylenated with 2.2 mol of ethylene oxide, sodium cocoyl isethionate and sodium α-($C_{14}$-$C_{16}$) olefin sulphonate, and mixtures thereof, with:

either an amphoteric surfactant such as the amine derivatives known as disodium cocoamphodipropionate or sodium cocoamphopropionate sold especially by the company Rhodia Chimie under the trade name "Miranol® C2M CONC" as an aqueous solution comprising 38% active material, or under the name Miranol® C32;

or an amphoteric surfactant such as alkylbetaines, such as the cocobetaine sold under the name "Dehyton® AB 30" as an aqueous solution comprising 32% AM by the company Cognis, or ($C_8$-$C_{20}$)alkylamido($C_1$-$C_6$)alkylbetaines, for example, Tegobetaine® F50 sold by the company Goldschmidt.

The composition may also comprise at least one additive chosen from antidandruff and anti-seborrhoeic agents, fragrances, nacreous agents, hydroxy acids, electrolytes, preserving agents, silicone and non-silicone sunscreens, vitamins, provitamins such as panthenol, anionic and nonionic polymers, proteins, protein hydrolysates, 18-methyleicosanoic acid, synthetic oils such as polyolefins, mineral oils, plant oils, fluoro oils and perfluoro oils, natural and synthetic waxes, compounds of ceramide type, carboxylic acid esters, silicones other than those of formulae (I) and (II), and also mixtures of these various compounds and any other additive usually used in cosmetics that does not affect the properties of the compositions.

These additives are present in the composition in proportions that may range from 0 to 20% by weight relative to the total weight of the composition. The amount of each additive is readily determined by a person skilled in the art, depending on its nature and its function.

The compositions may be used, for example, for washing or treating keratin materials such as the hair, the skin, the eyelashes, the eyebrows, the nails, the lips or the scalp.

In one embodiment, the compositions are detergent compositions such as shampoos, shower gels and bubble baths. In this embodiment, the compositions comprise at least one washing base, which is generally aqueous.

The at least one washing base comprises at least one surfactant. The at least one surfactant may be chosen, without discrimination, alone or as mixtures, from the anionic, amphoteric and nonionic surfactants as defined above.

The quantity and quality of the washing base are those that are sufficient to be able to give the final composition satisfactory foaming power and/or detergent power.

Thus, the washing base can be in an amount ranging, for example, from 4% to 50% by weight, such as from 6% to 35% by weight and further such as from 8% to 25% by weight, relative to the total weight of the final composition.

Another new embodiment is a process for treating a keratin material such as the skin or the hair, characterized in that the process comprises applying to the keratin material a cosmetic composition as defined above, and then optionally rinsing it out with water.

This process can allow the maintenance of the hairstyle and the treatment, care and washing or the removal of makeup from the skin, the hair or any other keratin material.

The compositions may also be in the form of rinse-out or leave-in conditioners, permanent-waving, hair-straightening, dyeing or bleaching compositions, or in the form of rinse-out compositions to be applied before or after dyeing, bleaching, permanent-waving or straightening the hair or between the two steps of a permanent-waving or hair-straightening operation.

When the composition is in the form of a conditioner, such as a rinse-out conditioner, it, for example, comprises at least one cationic surfactant, and its concentration ranges, for example, from 0.1% to 10% by weight, and such as from 0.5% to 5% by weight, relative to the total weight of the composition.

The compositions may also be in the form of washing compositions for the skin, such as in the form of bath or shower solutions or gels or makeup-removing products.

The compositions may also be in the form of aqueous or aqueous-alcoholic lotions for skincare and/or haircare.

The cosmetic compositions may be in the form of a gel, a milk, a cream, an emulsion, a thickened lotion or a mousse and may be used for the skin, the nails, the eyelashes, the lips and, for example, the hair.

The compositions may be packaged in various forms, such as in vaporizers, pump-dispenser bottles or in aerosol containers to allow the composition to be applied in vaporized form or in the form of a mousse. Such packaging forms are indicated, for example, when it is desired to obtain a spray, a lacquer or a mousse for treating a keratin material, such as the hair.

Throughout the text hereinabove and hereinbelow, the percentages expressed are on a weight basis.

New embodiments will now be illustrated more fully with the aid of the examples that follow, which cannot be considered as limiting it to the specific embodiments described.

In the examples, AM means active material.

EXAMPLE 1

A rinse-out conditioner having the composition below was prepared:

|  | in g AM |
|---|---|
| Hydroxypropyl corn distarch phosphate | 3.1 |
| Hydroxyethylcellulose | 0.6 |
| Oxyethylenated (40 EO) hydrogenated castor oil | 0.5 |
| Polydimethylsiloxane of formula (II) sold by Wacker under the name SLM 28020 | 2 |
| Fragrance | qs |
| Preserving agents | qs |
| Demineralized water | qs 100 g |

Hair treated with this conditioner has long-lasting softness and smoothness.

EXAMPLE 2

A rinse-out conditioner having the composition below was prepared:

|  | in g AM |
|---|---|
| Ethyltrimethylammonium methacrylate chloride homopolymer as a crosslinked inverse emulsion (Salcare SC 96 from Ciba) | 0.5 |
| Hydroxypropyl corn distarch phosphate | 3 |
| Oxyethylenated (40 EO) hydrogenated castor oil | 0.5 |
| Polydimethylsiloxane of formula (II) sold by Wacker under the name SLM 28020 | 2 |
| Fragrance | qs |
| Preserving agents | qs |
| Demineralized water | qs 100 g |

Hair treated with this composition has long-lasting softness and smoothness.

EXAMPLE 3

A rinse-out conditioner having the composition below was prepared:

|  | in g AM |
|---|---|
| SMDI/polyethylene glycol polymer containing decyl end groups (Aculyn 44 from Rohm & Haas) | 1 |
| Ethyltrimethylammonium methacrylate chloride homopolymer as a crosslinked inverse emulsion (Salcare SC 96 from Ciba) | 0.2 |
| Oxyethylenated (40 EO) hydrogenated castor oil | 0.5 |
| Polydimethylsiloxane of formula (II) sold by Wacker under the name SLM 28020 | 2 |
| Fragrance | qs |
| Preserving agents | qs |
| Demineralized water | qs 100 g |

Hair treated with this composition has long-lasting softness and smoothness.

EXAMPLE 4

A leave-in care mousse presented in aerosol form was prepared with 95 g of the composition of Example 3 and 5 g of isobutane/propane/butane (56/24/20) propellant Propel 45 from the company Repsol.

Hair treated with this mousse has long-lasting softness and smoothness.

EXAMPLE 5

A leave-in conditioner having the composition below was prepared:

|  | in g AM |
|---|---|
| Hydroxypropyl corn distarch phosphate | 4.4 |
| Cetyl alcohol | 0.8 |
| Cetylstearyl alcohol/oxyethylenated (20 EO)cetylstearyl alcohol | 0.8 |
| Oxyethylenated (20 EO) sorbitan monolaurate | 0.5 |
| Oxyethylenated (40 EO) hydrogenated castor oil | 0.4 |
| Polydimethylsiloxane of formula (II) sold by Wacker under the name SLM 28020 | 2 |
| Fragrance | qs |
| Preserving agents | qs |
| Demineralized water | qs 100 g |

Hair treated with this leave-in care product has long-lasting softness and smoothness.

EXAMPLE 6

A shampoo having the composition below was prepared:

|  | in g AM |
|---|---|
| Sodium lauryl ether sulphate (70/30 C12/C14) with 2.2 mol of ethylene oxide, containing 70% AM | 7 |
| Cocoylbetaine | 2.5 |
| Ethylene glycol distearate | 1.5 |
| Polydimethylsiloxane of formula (II) sold by Wacker under the name SLM 28020 | 1.5 |
| Polydimethylsiloxane of viscosity 60 000 cSt (DC200-60 000 cSt from Dow Corning) | 1 |
| Hydroxyethylcellulose quaternized with 2,3-epoxypropyltrimethylammonium chloride, sold under the name Ucare Polymer JR-400 by the company Amerchol | 0.4 |
| Acrylic polymer in emulsion form, sold under the name Aqua SF1 by Noveon | 0.8 |
| Preserving agents | qs |
| pH agents qs | pH 5.0 |
| Demineralized water qs | 100 |

Hair treated with this shampoo has long-lasting softness and smoothness.

Similar results may be obtained by replacing the 1.5 g AM of polydimethylsiloxane of formula (II) with 1 g AM of polydimethylsiloxane of formula (I) sold by Wacker under the name Belsil ADM 652.

The invention claimed is:
1. A cosmetic composition comprising, in a cosmetically acceptable medium, at least one thickener chosen from:
 (i) associative thickeners;
 (ii) crosslinked acrylic acid homopolymers;

(iii) crosslinked copolymers of (meth)acrylic acid and of ($C_1$-$C_6$)alkyl acrylate;
(iv) nonionic homopolymers and copolymers comprising ethylenically unsaturated monomers of ester and/or amide type;
(v) ammonium acrylate homopolymers and copolymers of ammonium acrylate and of acrylamide;
(vi) polysaccharides; and
(vii) $C_{12}$-$C_{30}$ fatty alcohols,
and at least one aminosilicone chosen from aminosilicones of formulae (I) and (II) below:

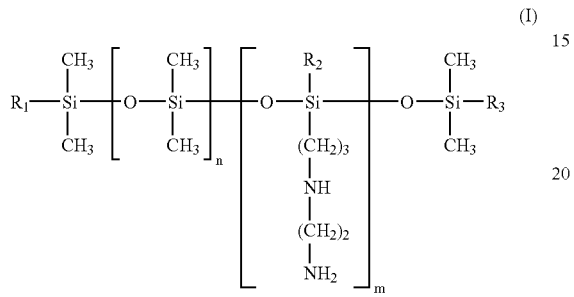

(I)

in which:
m and n are numbers such that the sum (n+m) ranges from 1 to 1000,
n is a number ranging from 0 to 999 and m is a number ranging from 1 to 1000;
$R_1$, $R_2$ and $R_3$, which may be identical or different, are chosen from hydroxyl and $C_1$-$C_4$ alkoxy radicals, wherein at least one of the radicals $R_1$, $R_2$ and $R_3$ is chosen from $C_1$-$C_4$ alkoxy radicals; and

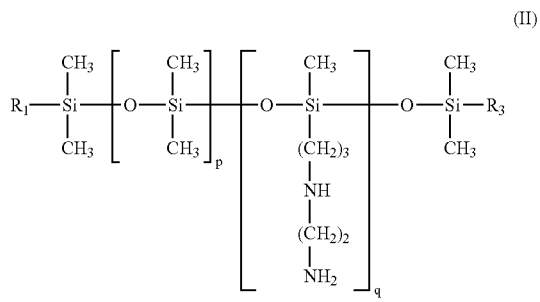

(II)

in which:
p and q are numbers such that the sum (p+q) ranges from 1 to 1000,
p is a number ranging from 0 to 999 and q is a number ranging from 1 to 1000;
$R_1$ and $R_2$, which are different, are chosen from hydroxyl and $C_1$-$C_4$ alkoxy radicals,
wherein at least one of the radicals $R_1$ and $R_2$ is chosen from $C_1$-$C_4$ alkoxy radicals.

2. The composition according to claim 1, wherein the associative thickeners are associative polymers chosen from:
(i) nonionic amphiphilic polymers comprising at least one fatty chain and at least one hydrophilic unit;
(ii) anionic amphiphilic polymers comprising at least one hydrophilic unit and at least one fatty-chain unit;
(iii) cationic amphiphilic polymers comprising at least one hydrophilic unit and at least one fatty-chain unit; and (iv) amphoteric amphiphilic polymers comprising at least one hydrophilic unit and at least one fatty-chain unit; the fatty chain comprising from 10 to 30 carbon atoms.

3. The composition according to claim 2, wherein the nonionic amphiphilic polymers comprising at least one fatty chain and at least one hydrophilic unit are chosen from:
(1) celluloses modified with groups comprising at least one fatty chain;
(2) hydroxypropyl guars modified with groups comprising at least one fatty chain;
(3) polyether urethanes comprising at least one fatty chain;
(4) copolymers of vinylpyrrolidone and of fatty-chain hydrophobic monomers;
(5) copolymers of monomers chosen from $C_1$-$C_6$ alkyl acrylates and methacrylates and of amphiphilic monomers comprising at least one fatty chain; and
(6) copolymers of hydrophilic monomers chosen from acrylates and methacrylates and of hydrophobic monomers comprising at least one fatty chain.

4. The composition according to claim 3, wherein in (3) the at least one fatty chain is chosen from $C_{10}$-$C_{30}$ alkyl and $C_{10}$-$C_{30}$ alkenyl groups.

5. The composition according to claim 3 wherein in (5) the copolymers are methyl methacrylate/stearyl acrylate copolymers.

6. The composition according to claim 3 wherein in (6) the copolymers are polyethylene glycol methacrylate/lauryl methacrylate copolymers.

7. The composition according to claim 2, wherein the anionic amphiphilic polymers comprising at least one hydrophilic unit and at least one fatty-chain unit are chosen from polymers comprising at least one fatty-chain allyl ether unit and at least one hydrophilic unit comprising an unsaturated ethylenic anionic monomer, polymers comprising at least one hydrophilic unit of unsaturated olefinic carboxylic acid type and at least one hydrophobic unit comprising a monomer chosen from ($C_{10}$-$C_{30}$) alkyl esters of unsaturated carboxylic acids, and methacrylic acid/methyl acrylate/ethoxylated alkyl dimethylmeta- isopropenylbenzylisocyanate copolymers.

8. The composition according to claim 2, wherein the cationic amphiphilic polymers comprising at least one hydrophobic unit and at least one fatty chain unit are chosen from quaternized cellulose derivatives and polyacrylates comprising amino side groups.

9. The composition according to claim 2, wherein the amphoteric amphiphilic polymers comprising at least one hydrophobic unit and at least one fatty-chain unit are chosen from methacrylamidopropyltrimethylammonium chloride/acrylic acid/$C_{10}$-$C_{30}$ alkyl methacrylate copolymers.

10. The composition according to claim 1, wherein the polysaccharides are chosen from glucans, modified and unmodified starches, amylose, amylopectin, glycogen, dextrans, celluloses and derivatives thereof, mannans, xylans, lignins, arabans, galactans, galacturonans, chitin, chitosans, glucuronoxylans, arabinoxylans, xyloglucans, glucomannans, pectic acids and pectins, alginic acid and alginates, arabinogalactans, carrageenans, agars, glycosaminoglucans, gum arabics, gum tragacanths, ghatti gums, karaya gums, carob gums, galactomannans and nonionic derivatives thereof and xanthan gums, and mixtures thereof.

11. The composition according to claim 10, wherein the galactomannans are chosen from guar gums and non-ionic derivatives thereof are chosen from hydroxypropyl guars.

12. A method for washing or caring for a keratin material comprising applying to the keratin material a composition comprising, in a cosmetically acceptable medium, at least one thickener and at least one aminosilicone chosen from aminosilicones of formulae (I) and (II) below:

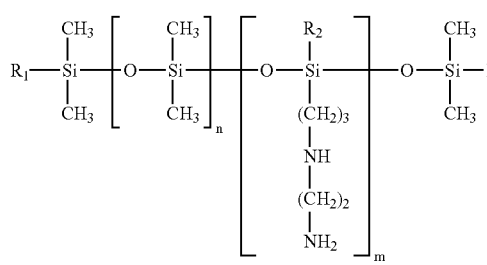

(I)

in which:
m and n are numbers such that the sum (n+m) ranges from 1 to 1000,
n is a number ranging from 0 to 999 and m is a number ranging from 1 to 1000;
$R_1$, $R_2$ and $R_3$, which may be identical or different, are chosen from hydroxyl and $C_1$-$C_4$ alkoxy radicals, wherein at least one of the radicals $R_1$, $R_2$ and $R_3$ is chosen from $C_1$-$C_4$ alkoxy radicals; and

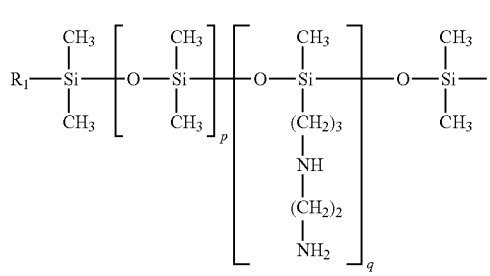

(II)

in which:
p and q are numbers such that the sum (p+q) ranges from 1 to 1000,
p is a number ranging from 0 to 999 and q is a number ranging from 1 to 1000;
$R_1$ and $R_2$, which are different, are chosen from hydroxyl and $C_1$-$C_4$ alkoxy radicals,
wherein at least one of the radicals $R_1$ and $R_2$ is chosen from $C_1$-$C_4$ alkoxy radicals.

13. A process for treating a keratin material, comprising applying to the keratin material a cosmetic composition comprising, in a cosmetically acceptable medium, at least one thickener and at least one aminosilicone chosen from aminosilicones of formulae (I) and (II) below:

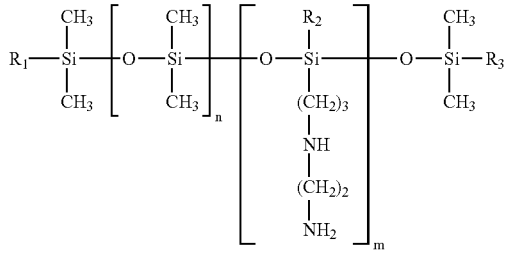

(I)

in which:
m and n are numbers such that the sum (n+m) ranges from 1 to 1000,
n is a number ranging from 0 to 999 and m is a number ranging from 1 to 1000;
$R_1$, $R_2$ and $R_3$, which may be identical or different, are chosen from hydroxyl and $C_1$-$C_4$ alkoxy radicals, wherein at least one of the radicals $R_1$, $R_2$ and $R_3$ is chosen from $C_1$-$C_4$ alkoxy radicals; and

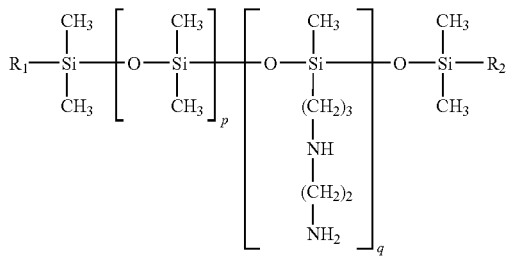

(II)

in which:
p and q are numbers such that the sum (p+q) ranges from 1 to 1000,
p is a number ranging from 0 to 999 and q is a number ranging from 1 to 1000;
$R_1$ and $R_2$, which are different, are chosen from hydroxyl and $C_1$-$C_4$ alkoxy radicals,
wherein at least one of the radicals $R_1$ and $R_2$ is chosen from $C_1$-$C_4$ alkoxy radicals; and
then optionally rinsing the keratin material with water.

14. The process according to claim 13, wherein the keratin material is hair.

15. A process for conditioning a keratin material comprising applying to the keratin material a composition comprising, in a cosmetically acceptable medium, at least one thickener and at least one aminosilicone chosen from aminosilicones of formulae (I) and (II) below:

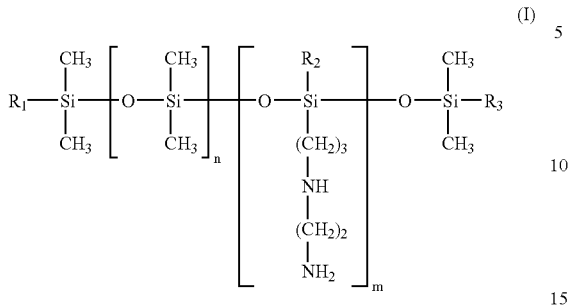

(I)

in which:
- m and n are numbers such that the sum (n+m) ranges from 1 to 1000,
- n is a number ranging from 0 to 999 and m is a number ranging from 1 to 1000;
- $R_1$, $R_2$ and $R_3$, which may be identical or different, are chosen from hydroxyl and $C_1$-$C_4$ alkoxy radicals, wherein at least one of the radicals $R_1$, $R_2$ and $R_3$ is chosen from $C_1$-$C_4$ alkoxy radicals; and

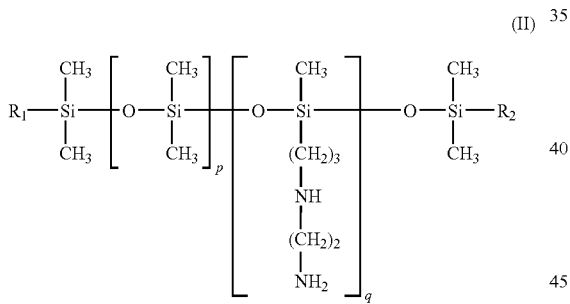

(II)

in which:
- p and q are numbers such that the sum (p+q) ranges from 1 to 1000,
- p is a number ranging from 0 to 999 and q is a number ranging from 1 to 1000;
- $R_1$ and $R_2$, which are different, are chosen from hydroxyl and $C_1$-$C_4$ alkoxy radicals,
- wherein at least one of the radicals $R_1$ and $R_2$ is chosen from $C_1$-$C_4$ alkoxy radicals.

16. A method for improving lightness, softness, sheen and/or disentangling and/or facilitating styling of a keratin material, comprising applying to the keratin material a composition comprising, in a cosmetically acceptable medium, at least one thickener and at least one aminosilicone chosen from aminosilicones of formulae (I) and (II) below:

(I)

in which:
- m and n are numbers such that the sum (n+m) ranges from 1 to 1000,
- n is a number ranging from 0 to 999 and m is a number ranging from 1 to 1000;
- $R_1$, $R_2$ and $R_3$, which may be identical or different, are chosen from hydroxyl and $C_1$-$C_4$ alkoxy radicals, wherein at least one of the radicals $R_1$, $R_2$ and $R_3$ is chosen from $C_1$-$C_4$ alkoxy radicals; and (II)

in which:
- p and q are numbers such that the sum (p+q) ranges from 1 to 1000,
- p is a number ranging from 0 to 999 and q is a number ranging from 1 to 1000;
- $R_1$ and $R_2$, which are different, are chosen from hydroxyl and $C_1$-$C_4$ alkoxy radicals,
- wherein at least one of the radicals $R_1$ and $R_2$ is chosen from $C_1$-$C_4$ alkoxy radicals.

17. A method for improving remanence of conditioning effects of a keratin material with respect to shampooing, comprising applying to the keratin material a composition comprising, in a cosmetically acceptable medium, at least one thickener and at least one aminosilicone chosen from aminosilicones of formulae (I) and (II) below:

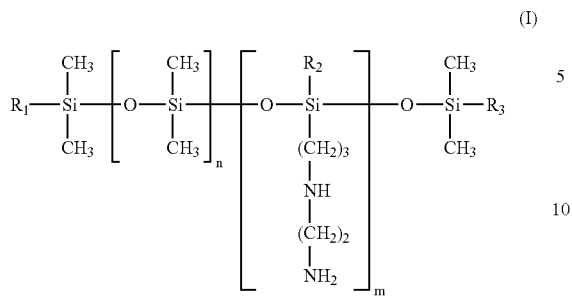 (I)

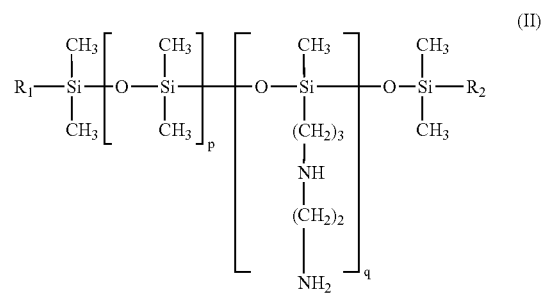 (II)

in which:
- m and n are numbers such that the sum (n+m) ranges from 1 to 1000,
- n is a number ranging from 0 to 999 and m is a number ranging from 1 to 1000;
- $R_1$, $R_2$ and $R_3$, which may be identical or different, are chosen from hydroxyl and $C_1$-$C_4$ alkoxy radicals, wherein at least one of the radicals $R_1$, $R_2$ and $R_3$ is chosen from $C_1$-$C_4$ alkoxy radicals; and in which:
- p and q are numbers such that the sum (p+q) ranges from 1 to 1000,
- p is a number ranging from 0 to 999 and q is a number ranging from 1 to 1000;
- $R_1$ and $R_2$, which are different, are chosen from hydroxyl and $C_1$-$C_4$ alkoxy radicals,
- wherein at least one of the radicals $R_1$ and $R_2$ is chosen from $C_1$-$C_4$ alkoxy radicals.

* * * * *